United States Patent [19]

Eaton et al.

[11] Patent Number: 5,723,592
[45] Date of Patent: Mar. 3, 1998

[54] PARALLEL SELEX

[75] Inventors: Bruce E. Eaton; Larry Gold, both of Boulder, Colo.

[73] Assignee: NeXstar Pharmaceuticals, Inc., Boulder, Colo.

[21] Appl. No.: 462,389

[22] Filed: Jun. 5, 1995

Related U.S. Application Data

[60] Division of Ser. No. 309,245, Sep. 20, 1994, which is a continuation-in-part of Ser. No. 714,131, Jun. 10, 1991, Pat. No. 5,475,096, which is a continuation-in-part of Ser. No. 536,428, Jun. 11, 1990, abandoned.

[51] Int. Cl.$^6$ .................. C07H 21/04; C07H 21/02; C12Q 1/68
[52] U.S. Cl. .................. 536/23.1; 435/6; 935/77; 935/78
[58] Field of Search .................. 536/23.1; 435/6; 935/77, 78

[56] References Cited

U.S. PATENT DOCUMENTS

| | | | |
|---|---|---|---|
| 4,794,073 | 12/1988 | Daztagupta et al. | 435/6 |
| 5,270,163 | 12/1993 | Gold et al. | 435/6 |

FOREIGN PATENT DOCUMENTS

| | | |
|---|---|---|
| 2 183 661 | 6/1987 | United Kingdom. |
| WO91/14696 | 10/1991 | WIPO. |
| WO91/19813 | 12/1991 | WIPO. |
| WO92/14843 | 9/1992 | WIPO. |
| WO95/16788 | 6/1995 | WIPO. |
| WO96/06944 | 3/1996 | WIPO. |

OTHER PUBLICATIONS

Alper (1994) Science 264:1399.
Bartel and Szostak (1993) Science 261:1411.
Brenner and Lerner (1992) Proc. Natl. Acad. Sci. USA 89:5381.
Cech (1987) Science 236:1532.
Fodor et al. (1991) Science 251:767.
Longman (1994) In Vivo 23–31.
Lorsch and Szostak (1994) Nature 371:31.
McCorkle and Altman (1987) J. Chem. Education 64:221.
Needels et al. (1993) Proc. Natl. Acad. Sci. USA 90:10700.
Ohlmeyer et al. (1993) Proc. Natl. Acad. Sci. USA 90:10922.
Piccirilli et al. (1992) Science 256:1420.
Prudent et al. (1994) Science 264:1924.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci USA 63:805.
Levisohn and Spiegelman Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

This invention discloses a method for coevolving products from two or more reactants, along with the nucleic acid that can facilitate the reaction for making the products. The invention further discloses the products and facilitating nucleic acids produced by said method.

4 Claims, 12 Drawing Sheets

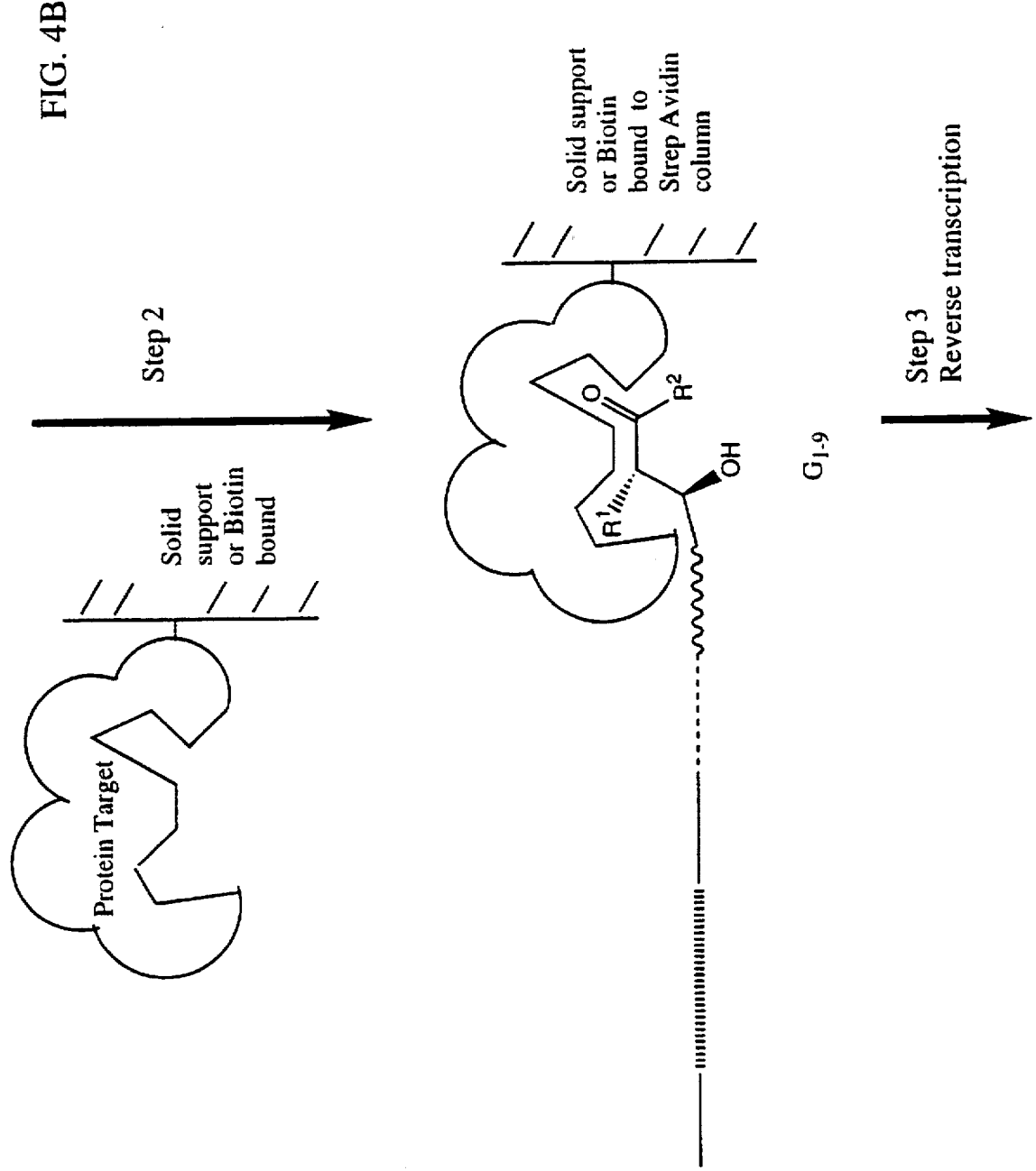

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 10
( B ) TYPE: nucleic acid
( C ) STRANDEDNESS: single
( D ) TOPOLOGY: linear ( x i ) SEQUENCE DESCRIPTION: SEQ ID NO:1:

CCAGGCACGC 10

( 2 ) INFORMATION FOR SEQ ID NO:2:

( i ) SEQUENCE CHARACTERISTICS:
( A ) LENGTH: 87
( B ) TYPE: nucleic acid
( C ) STRANDEDNESS: single
( D ) TOPOLOGY: linear ( x i ) SEQUENCE DESCRIPTION: SEQ ID NO:2:

GGGAGACAAG AATAAACGCT CAANNNNNNN NNNNNNNNNN NNNNNNNNNN NNNNNNNNNN 60

NNNTTCGACA GGAGGCTCAC AACAGGC 87

( 2 ) INFORMATION FOR SEQ ID NO:3:

( i ) SEQUENCE CHARACTERISTICS:
( A ) LENGTH: 20
( B ) TYPE: nucleic acid
( C ) STRANDEDNESS: single
( D ) TOPOLOGY: linear ( x i ) SEQUENCE DESCRIPTION: SEQ ID NO:3:

CTTGTCTCCC GCGTGCCTGG 20

PARALLEL SELEX

RELATED APPLICATIONS

This application is a divisional of U.S. patent application Ser. No. 08/309,245, filed Sep. 20, 1994, entitled Parallel SELEX, which is a Continuation-In-Part of U.S. patent application Ser. No. 07/714,131, filed Jun. 10, 1991, entitled Nucleic Acid Ligands, (now U.S. Pat. No. 5,475,096), which is a Continuation-In-Part of U.S. patent Application Ser. No. 07/536,428, filed Jun. 11, 1990, entitled Systematic Evolution of Ligands by Exponential Enrichment, now abandoned.

FIELD OF THE INVENTION

This invention relates to methods for producing products from two or more reactants wherein the reaction, preferably bond formation, between the reactants is mediated by a nucleic acid having facilitating properties. Also included in the invention are the products made by the methods. More particularly, the invention relates to methods for coevolving a facilitating nucleic acid and the product that is assembled by the mediation of said facilitating nucleic acid. The invention further relates to a method for identifying nucleic acids having facilitative properties and said nucleic acids.

BACKGROUND OF THE INVENTION

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled Systematic Evolution of Ligands by Exponential Enrichment, now abandoned, U.S. patent application Ser. No. 07/714,131, filed Jun. 10, 1991, entitled Nucleic Acid Ligands, (now U.S. Pat. No. 5,475,096) U.S. patent application Ser. No. 07/931,473, filed Aug. 17, 1992, entitled Nucleic Acid Ligands, now U.S. Pat. No. 5,270,163 (see also PCT/US91/04078) (WO91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

It has been recognized by the present inventors that the SELEX method demonstrates that nucleic acids as chemical compounds can form a wide array of shapes, sizes and configurations, and are capable of a far broader repertoire of binding and other functions than those displayed in biological systems.

The dogma for many years was that nucleic acids had primarily an informational role. Through the application of SELEX it has become clear to the present inventors that nucleic acids have three dimensional structural diversity not unlike proteins. As such, the present inventors have recognized that SELEX or SELEX-like processes could be used to identify nucleic acids which can facilitate any chosen reaction in that nucleic acid ligands can be identified for any given target. In theory, within a candidate mixture of approximately $10^{13}$ to $10^{18}$ nucleic acids, the present inventors postulate that at least one nucleic acid exists with the appropriate shape to facilitate a broad variety of physical and chemical interactions.

Studies to date have identified only a few nucleic acids which have only a narrow subset of facilitating capabilities. A few RNA catalysts are known (Cech, 1987.*Science* 236:1532–1539 and McCorkle Altman (1987) *J. Chem. Education* 64:221–226). These naturally occurring RNA enzymes (ribozymes) have to date only been shown to act on oligonucleotide substrates. Further, these molecules perform over a narrow range of chemical possibilities, which are thus far related largely to phosphodiester bond condensation/hydrolysis, with the exception of the possible involvement of RNA in protein biosynthesis. Despite intense recent investigation to identify RNA or DNA catalysts, few successes have been identified. Phosphodiester cleavage, hydrolysis of aminoacyl esters (Piccirilli et at., 1992. *Science* 256:1420–1424), ligation of an oligonucleotide with a 3' OH to the 5' triphosphate end of the catalyst (Bartel and Szostak 1993. *Science* 261:1411–1418), biphenyl isomerase activity (Prudent et al. (1994). *Science* 264:1924–1927), and polynucleotide kinase activity (Lorsch and Szostak 1994). *Nature* 371:31–36) have been observed. The nucleic acid catalysts known to date have certain shortcomings associated with their effectiveness in bond forming/breaking reactions. Among the drawbacks are that they act slowly relative to protein enzymes, and as described above, they perform over a somewhat narrow range of chemical possibilities.

The basic SELEX method has been modified to achieve a number of specific objectives. For example, U.S. patent application Ser. No. 07/960,093, filed Oct. 14, 1992, entitled Method for Selecting Nucleic Acids on the Basis of Structure, describes the use of SELEX in conjunction with gel electrophoresis to select nucleic acid molecules with specific structural characteristics, such as bent DNA. U.S. patent application Ser. No. 08/123,935, filed Sep. 17, 1993, entitled Photoselection of Nucleic Acid Ligands describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled High-Affinity Nucleic Acid Ligands That Discriminate Between Theophylline and Caffeine, describes a method for identifying highly specific nucleic acid ligands able to discriminate between closely related molecules, termed Counter-SELEX. U.S. patent application Ser. No. 08/143,564, filed Oct. 25, 1993, entitled Systematic Evolution of Ligands by EXponential Enrichment: Solution SELEX, describes a SELEX-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled High Affinity Nucleic Acid Ligands Containing Modified Nucleotides, that describes oligonucleotides containing nucleotide derivatives chemically modified at the 5-and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled Novel Method of Known and Novel Preparation of 2' Modified Nucleosides by Intramolecular Nucleophilic Displacement, describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled Systematic Evolution of Ligands by Exponential Enrichment: Chimeric SELEX and U.S. patent application Ser. No. 08/234,997, filed Apr. 28, 1994, entitled Systematic Evolution of Ligands by Exponential Enrichment: Blended SELEX, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Recently some attempts have been made to use combinatorial chemistry as a way to discover new drugs. A few elaborate schemes have been devised to produce combinatorial libraries having an array of different structures. The structures associated with known combinatorial libraries include nucleic acids as described previously for the SELEX process, peptides (Brenner and Lerner (1992) *Proc. Natl. Acad. Sci. USA* 89:5381–5383; Needels, et al., 1993. Proc. Natl. Acad. Sci. USA 90:10700–10704; Alper, 1994. *Science* 264:1399–1401; Longman, 1994. In Vivo 23–31, Fodor et al., 1991. *Science* 251:767–773), and a much smaller number directed to small organic molecules (Ohlmeyer, et al., 1993. *Proc. Natl. Acad. Sci. USA* 90:10922–10926). There are certain drawbacks associated with each of the known combinatorial library approaches.

First, some of the schemes used for preparing peptide or small molecule combinatorial libraries require rigorous recordkeeping systems to keep track of which chemistries occurred at any point in the array/matrix. Moreover, peptides and small organic molecules are not amplifiable and therefore relatively large quantifies of each individual product must be present in the library to enable testing and identification of desirable products. In order to obtain large enough quantities of specific products, the reactions that make up the array must be highly efficient. More importantly, for these approaches to work, it is not possible to have a mixture of products and side products at the same site in the array. Diversity is generated by polymeric combination of multiple steps, each of which consists of a single reaction with a predictable outcome. However, the extent of polymeric combination is limited by yield and recordkeeping constraints.

Another limitation of small molecule combinatorial approaches is that the schemes generally exclude bond formation reactions that produce new stereocenters by asymmetric reactions. By eliminating asymmetric reactions, these approaches do not provide chemical diversity that can be generated at a single step. Often, asymmetric reactions are difficult to control, so if reactions that form new chiral centers are included in the combinatorial scheme, it would be likely that racemic product mixtures would result. Racemic product mixtures can result in background problems. For example, it is possible that the ideal atoms and groups are introduced for assembly, but that the chirality of the product is crucial to the desired properties and the correct enantiomer is only present as a small percentage of the total. In this example, it is quite likely that the correct enantiomer will not be made in a quantity sufficient to be identified. Further, it is impossible to accurately predict the chirality of each individual reaction when a large array of reactants is included in an asymmetric transformation. Therefore, it is unlikely that the difficulty associated with racemic mixtures can be overcome by traditional means. The labor and time necessary to include asymmetric catalysis in conventional combinatorial library approaches is generally impractical. Therefore, asymmetric reactions are generally excluded to circumvent the described problems.

Nevertheless, asymmetric reactions include one of the most powerful of all bond forming reaction types. The absence of asymmetric reactions in combinatorial library approaches significantly limits the types of products that can be made and the breadth of the library. The following example illustrates the immense diversity afforded by asymmetric reactions. In general, the number of potential products produced from a matrix of reactants is $M \times 2^n$ where M=the number of reactants and n=the number of chiral centers. Consider a matrix comprised of bond forming reactions where one asymmetric bond is formed. The number of potential products increases as two times the product of the matrix. Note that for each bond formed the possibility exists to generate two chiral centers, so that for a single transformation the number of possible combinations is 4 or $2^2$. Consider a specific example of an asymmetric reaction, the Diels-Alder reaction, where two carbon- carbon bonds are formed and the potential for producing 4 chiral centers exists.

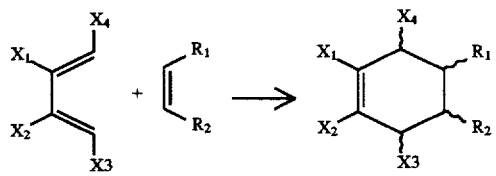

For the Diels-Alder reaction, the relative stereochemistry of the two ends of the dienophile reactant are coupled as are the two ends of the diene reactant, reducing the number of possibilities to $2^3$ for each diene/dienophile pair. This means that for a single dienophile in combination with 10 dienes, the number of possible product molecules that could be formed is $1 \times 10 \times 2^3 = 80$ (1 first reactant and 80 second reactants). To get the same level of diversity from traditional combinatorial approaches using only a single bond forming step would require the direct synthesis of 81 compounds. For an array of 10×10 reactants, the standard combinatorial approach yields 100 compounds. Expansion of the asymmetric Diels-Alder reaction array to 10×10 reactants has the potential to yield 800 new compounds from the original 20. Current combinatorial strategies cannot screen for all potential products of asymmetric transformations because it is generally not possible to obtain each of the products desired. As described above, the elimination of asymmetric reactions is a serious limitation of conventional combinatorial library approaches.

An ideal combinatorial library approach would be complementary to the SELEX method, where yield is not a concern, due to the ability to amplify the oligonucleotide products, and yet yield small organic molecules which are generally orally active and relatively inexpensive to produce. The present invention combines the power of SELEX with a novel approach for generating a large, structurally diverse library of products. The approach taken in the present invention overcomes many of the inadequacies associated with other combinatorial library approaches and represents a revolutionary concept in future drug discovery.

BRIEF SUMMARY OF THE INVENTION

The present invention provides product libraries which are evolved simultaneously with the corresponding nucleic acid facilitator required to produce each member of the library from one or more chemical reactants. More importantly, products can be identified from the product library which have predetermined desirable characteristics. This method, referred to herein as Parallel SELEX, is a SELEX-like process which is used to generate such a product library and subsequently to identify products with desired characteristics. As in the SELEX process, a huge, diverse nucleic acid test mixture is provided. Each nucleic acid is coupled to a chemical reactant. The invention is premised on the assumption that in a large enough nucleic acid library, one can identify nucleic acids in the nucleic acid test mixture capable of mediating a chemical reaction between the chemical reactant attached to the nucleic acid and a free chemical reactant. Further, among the subset of nucleic acids capable of mediating a chemical reaction, some are highly specific for generating each or a substantial portion of all the possible products. Therefore, the product library will contain at least some of all possible products for a given reaction. The nucleic acid provides facilitative specificity for the product and the product in turn provides specificity for a predetermined desirable action on a target.

Parallel SELEX alleviates many of the shortcomings of the prior art combinatorial library approaches. In its most basic form, Parallel SELEX comprises forming a product library by contacting two or more reactants wherein one of the reactants is coupled to a nucleic acid capable of mediating bond formation, selecting for products having predetermined desirable characteristics, and identifying the product using the power of the SELEX process for amplification. A schematic depiction of the Parallel SELEX process is provided in FIG. 1.

The invention provides a method for identifying a desirable product from a product library, wherein said desirable product is selected for its ability to perform a preselected function on a target, said method comprising: preparing a nucleic acid-reactant test mixture comprised of nucleic acids each having a region of randomized sequence and each being associated with a first reactant; reacting said nucleic acid-reactant test mixture with a free reactant to form a product library comprised of nucleic acids associated with a product formed by the reaction of said first and free reactants; and partitioning between members of said product library based on their relative ability to perform said preselected function, whereby said desirable products can be identified.

The invention provides a product library comprised of a mixture of products that are the result of a reaction between at least a coupled reactant and a free reactant, wherein said coupled reactant is attached to the nucleic acid that facilitated the reaction between said reactants.

Parallel SELEX does not require keeping track of a matrix of products and their respective chemistries nor does it require highly efficient or rapid reactions. This advantage is a result of the fact that product formation is directed by specific nucleic acids. This directed approach is contrasted with the encoded approach taken by other combinatorial library approaches. The nucleic acid that specifically facilitates the desirable product formation can be easily amplified and the product reliably reproduced in subsequent rounds of production. This method allows a multitude of reactions to take place initially which can be sorted out later once it has been determined that products which display predetermined desirable characteristics have been formed. By this method, products may be evolved in the absence of detailed structural information.

Parallel SELEX can include the formation of product libraries using asymmetric reactions. Unlike conventional combinatorial library approaches, even though it is impossible to predict the stereochemical outcome at the onset of the reaction, asymmetric reactions can be included. The specific chemistry does not have to be tracked for Parallel SELEX to be effective. The only requirement is that the nucleic acid mediate at least a finite subset of the total number of possible reactions.

In another embodiment, facilitative nucleic acids are provided. Nucleic acids having facilitative properties are capable of mediating chemical reactions such as bond formation or bond cleavage. The nucleic acids can be modified in various ways to include other chemical groups that provide additional charge, polarizability, hydrogen bonds, electrostatic interaction, and fluxionality which assist in chemical reaction mediation. The other chemical groups can include, inter alia, alkyl groups, amino acid side chains, various cofactors, and organometallic moieties. The invention requires that the facilitative nucleic acids direct the synthesis of products which have predetermined desirable characteristics.

Included in the invention are pharmaceutical compositions containing the inventive products and methods of administering the compositions. Also included are diagnostic reagents, agricultural compositions and manufacturing compositions containing the inventive products.

BRIEF DESCRIPTION OF THE FIGURES

FIGS. 4A–4C depict a schematic representation of the Parallel SELEX process wherein a facilitating nucleic acid mediates a generic bond forming Aldol condensation reaction between a ketone and an aldehyde.

DETAILED DESCRIPTION OF THE INVENTION

Parallel SELEX provides product libraries which are formed by combining a pool of first chemical reactants coupled to a nucleic acid with a pool of free chemical reactants. The coupled nucleic acid is capable of mediating the chemical reaction which leads to the product library and further the nucleic acid is amplifiable so a product which has a predetermined desirable characteristic can be enriched for and identified from the product library.

Figure 1:
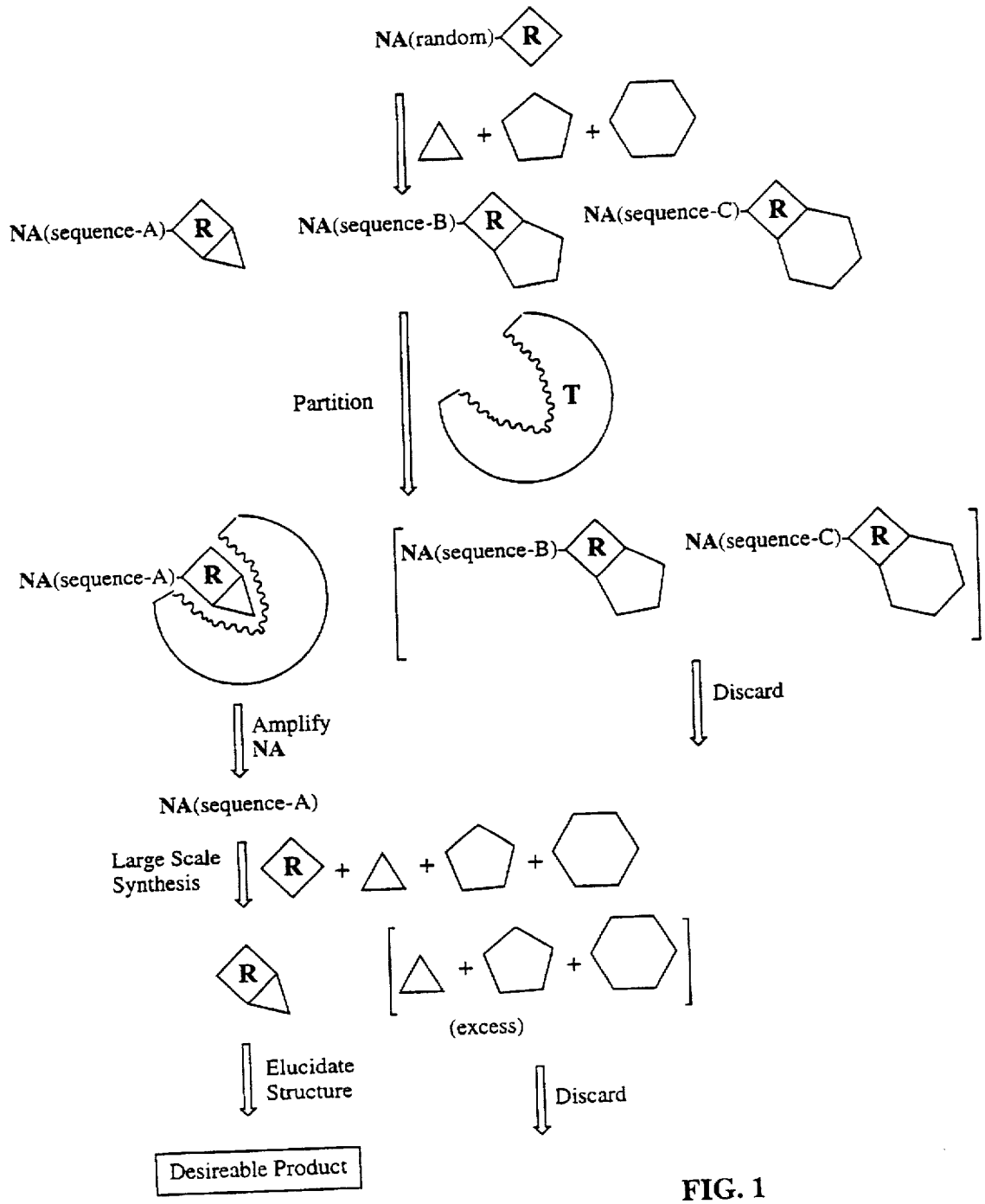
FIG. 1 depicts a schematic representation of the Parallel SELEX process in its most basic form.

In its most general form, Parallel SELEX may be described as in FIG. 1. A nucleic acid-reactant test mixture is formed by attaching a first reactant to each of the nucleic acids in a test mixture (containing $10^2$ to $10^{18}$ nucleic acids with randomized sequences). The nucleic acid-reactant test mixture is treated with other free reactants (denoted as triangle, pentagon and hexagon) that will combine with the first reactant (R) to form different products. It is important to note that from the nucleic acid test mixture (NA), discrete nucleic acid sequences will be associated with facilitating the formation of the different shaped products as denoted by sequence-A, sequence-B and sequence-C in FIG. 1. The products may differ in shape, reactivity or both shape and reactivity. Partitioning of the desirable product shape or reactivity is accomplished by binding to or reaction with a target. Proteins, small molecules, lipids, saccharides, etc., are all examples of targets (T). After binding to or reacting with the target the non-interacting products, which are attached to sequence-B and sequence-C as depicted in FIG. 1 are separated from sequence-A and discarded. The nucleic acid sequence-A is then amplified by a variety of methods known to those experienced in the art. Sequence-A is then used to facilitate the assembly of the desirable product by facilitating the specific reaction to form the selected product on treatment with the mixture of starting reactants. In a typical reaction, Sequence-A can be reattached to the first reactant, however, said reattachment is not always required. This is an idealized case and in many examples the nucleic acid facilitator may assemble more than one product from the starting mixture, but all of the products selected will have the desired properties of binding to or chemical reaction with the target.

I. DEFINITIONS

Certain terms used to describe the invention herein are defined as follows:

"Nucleic acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the individual nucleic acid bases or to the nucleic acid as a whole. Such modifications include, but are not limited to, modified bases such as 2'-position base modifications, 5-position pyrimidine modifications, 8-position purine modifications, modifications at cytosine exocyclic amines, substitution of 5-bromouracil; backbone modifications, methylations, unusual base-pairing combinations such as the isobases isocytidine and isoguanidine and the like. Modifications can also include 3' and 5' modifications such as capping. Modifications that occur after each round of amplification are also compatible with this invention. Post-amplification modifications can be reversibly or irreversibly added after each round of amplification. Virtually any modification of the nucleic acid is contemplated by this invention. The length of the randomized section of the nucleic acid is generally between 8 and 250 nucleotides, preferably between 8 and 60 nucleotides.

"Nucleic acid test mixture" is a mixture of nucleic acids of differing, randomized sequence including some which have a shape which enables them to mediate the formation and/or cleavage of chemical bonds. The source of a "nucleic acid test mixture" can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic acid having facilitating properties" or "facilitating nucleic acid" or "facilitative nucleic acid" or "nucleic acid facilitator" refers to any nucleic acid which is capable of mediating or facilitating a chemical reaction. The chemical reaction can be a formation or bond cleavage reaction. The preferred embodiments of this invention are directed to bond formation reactions. The nucleic acid does not necessarily need to show catalytic turnover to be considered to have facilitating properties. The reaction rate of product formation can be increased by the presence of the nucleic acid, however, increased reaction rate is not a requirement for facilitating properties. A facilitating nucleic acid folds such that its three-dimensional structure facilitates a specific chemical reaction. The nucleic acid can mediate the chemical reaction either alone, in combination with another catalytic moiety coupled directly with the nucleic acid, or in combination with another catalytic moiety which could be found in solution. The other catalytic moieties can include organometallic moieties, metal ions, etc. The nucleic acid can cause different stereoisomers to be formed. The nucleic acid can mediate formation or cleavage of a variety of bond types, including, but not Limited to, condensation/hydrolysis reactions, cycloaddition reactions (such as the Diels-Alder and Erie reaction), 1,3 dipolar conjugate addition to $\alpha,\beta$-unsaturated compounds, Aldol condensations, glycosylation of peptides, sugars and lipids. Additionally, when the nucleic acid modification includes an organometallic moiety, other reactions may occur which could form symmetric or asymmetric products, including, but not limited to, cyclopropanation, hydrogenation, cyclotrimerization of alkynes, [3+2] and [4+1] cycloaddition of unsaturated molecules, and olefin metathesis.

"Reactant" refers to any chemical entity that could be involved in a bond forming or bond cleavage reaction which is compatible with the thermal and chemical stability of nucleic acids, including the modifications described above. The term reactant may refer to a single chemical entity or a class of chemical compounds, including several reactants of several general chemical structures or several reactants of different general chemical structures. A reactant typically has a molecular weight in the range of 2 to 1000, preferably about 26 to 500. Particularly preferred reactants include small organic molecules such as alkenes, alkynes, alcohols, aldehydes, ketones, esters, carboxylic acids, aromatic carbocycles, heterocycles, dienes, thiols, sulfides, disulfides, epoxides, ethers, mines, imines, phosphates, amides, thioethers, sulfonates and halogenated compounds. Inorganic reactants are also contemplated by this invention. However, in some embodiments of the invention, larger reactants can be included, such as polymers or proteins. The selection of the chemical reactants used can be random or based on a number of criteria, including the nature of the product desired, the activity the product is meant to have, or information based on the nature of the target on which the product is meant to act. "Coupled Reactant" or "First Reactant" or "First Chemical Reactant" refers to those Reactants described above which are coupled to a nucleic acid to form a nucleic acid-reactant test mixture. The coupling of the first reactant to the nucleic acid can be either covalent or non-covalent. The first chemical reactant can be a single chemical entity or a class of chemical molecules, including several reactants of several general chemical structures or several reactants of different general chemical structures. For example, the first reactant may be one alkene (e.g., 1-propene), or 10 different alkenes, or 10 different alkenes and 10 different alkynes. "Free Reactant" or "Second Reactant" or "Free Chemical Reactant" refers to those Reactants that are not coupled to a nucleic acid. A reaction may involve more than one free reactant, as in a cyclotrimerization reaction. The free reactants may be the same or different from each other or from the coupled reactant. For example, the free reactant may be one alkene (e.g., 1-propene), or 10 different alkenes, or 10 different alkenes and 10 different alkynes.

"Nucleic acid-reactant test mixture" refers to the mixture of nucleic acids each of which has been coupled to a first chemical reactant. The coupling can be covalent or non-covalent, direct or with a linker between the nucleic acid and the reactant. The nucleic acid-reactant test mixture is contacted with a pool of free chemical reactants to enable the formation of a product library.

"Product" refers to a compound resulting from a bond forming or bond cleavage reaction between one or more reactants which has been mediated by a nucleic acid. In the preferred embodiment, a product is typically formed between a coupled reactant and a free reactant. Two reactants that react to make a product do not necessarily have to be reactants of different chemical structures. Preferably the products of this invention are small organic molecules that can be medicinally active and show therapeutic efficacy or are useful as diagnostic agents or agricultural agents. The typical molecular weight of a product is in the range of about 40 to 2000, preferably about 100 to 1000. However, in certain less preferred embodiments, the products can be larger molecules as illustrated by peptides, proteins, polymers, etc. In certain less preferred embodiments, the reaction is a bond cleavage reaction and can take place with only the coupled reactant or between two or more reactants.

"Product library" refers to the collection of products formed by the chemical reaction between a reactant coupled to a facilitating nucleic acid and preferably at least one free reactant. Due to the nature of the invention, a product library can contain many diverse products of varying chemical structures.

"Product having the ability to perform a preselected function on a target" or "Product having Predetermined Characteristic" or "Desirable Produce" refers to a product that acts on a target in a predetermined desirable manner. Examples of predetermined desirable actions on a target include, but are not limited to, binding of the target, catalytically changing the target, reacting with the target in a way which modifies/alters the target or the functional activity of the target, covalently attaching to the target as in a suicide inhibitor, facilitating the reaction between the target and another molecule. As one example, in a product library, a product having a predetermined characteristic is one which binds a target with greater affinity than that of the bulk population. In any given product library there can exist more than one product having a predetermined characteristic for a given target. The products having predetermined characteristics can differ from one another in their binding affinities for the target or in their other abilities to act on the target.

"Target" refers to any compound upon which a product identified by the Parallel SELEX method can act in a predetermined desirable manner. A target molecule can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc., without limitation.

"Partitioning" means any process whereby members of the nucleic acid test mixture or nucleic acid-reactant test mixture can be separated from the bulk of the test mixture based on the ability of the nucleic acid to facilitate a reaction involving its associated reactant, resulting in a desirable product. Partitioning can be accomplished by various methods known in the art. Filter binding, affinity chromatography, liquid-liquid partitioning, filtration, gel shift, density gradient centrifugation are all examples of suitable partitioning methods. The choice of partitioning method will depend on properties of the target and the product and can be made according to principles and properties known to those of ordinary skill in the art.

Additionally, it may be desirable as an initial partitioning step to partition between nucleic acids which are associated with products (and therefore facilitating nucleic acids) vs. those which are only associated with a first reactant (non-facilitating nucleic acids). This partitioning step can be accomplished by numerous methods known to one of ordinary skill in the art, such as sizing columns, affinity chromatography, etc. After such a partitioning step, the nucleic acid test mixture would be enriched for facilitating nucleic acids.

"Amplifying" means any process or combination of process steps that increases the amount or number of copies of a molecule or class of molecules. In preferred embodiments, amplification occurs after members of the test mixture have been partitioned, and it is the facilitating nucleic acid associated with a desirable product that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the mixture prior to amplification. It is known that many modifications to nucleic acids are compatible with enzymatic amplification. Modifications that are not compatible with amplification can be made after each round of amplification, if necessary.

"Randomized" is a term used to describe a segment of a nucleic acid having, in principle, any possible sequence over a given length. Randomized sequences will be of various lengths, as desired, ranging from about eight to more than one hundred nucleotides. The chemical or enzymatic reactions by which random sequence segments are made may not yield mathematically random sequences due to unknown biases or nucleotide preferences that may exist. The term "randomized" is used instead of "random" to reflect the possibility of such deviations from non-ideality. In the techniques presently known, for example sequential chemical synthesis, large deviations are not known to occur. For short segments of 20 nucleotides or less, any minor bias that might exist would have negligible consequences. The longer the sequences of a single synthesis, the greater the effect of any bias.

A bias may be deliberately introduced into a randomized sequence, for example, by altering the molar ratios of precursor nucleoside (or deoxynucleoside) triphosphates in the synthesis reaction. A deliberate bias may be desired, for example, to affect secondary structure, to introduce bias toward molecules known to have facilitating activity, to introduce certain structural characteristics, or based on preliminary results.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to amplify the nucleic acid associated with a desirable product.

"Parallel SELEX" is a method wherein nucleic acids in a nucleic acid test mixture are coupled to a chemical reactant which is then contacted with a pool of other free chemical reactants under conditions favorable for facilitated bond formation to produce a product library. The product library is screened to identify products having predetermined desirable characteristics. The product can be tested for its ability to act on a given target in the predetermined manner (e.g., bind to the target, modify the target in some way, etc.). The desirable products can then be partitioned away from the undesirable products. The desirable product remains coupled to the facilitating nucleic acid that directed its synthesis. The facilitating nucleic acid can be partitioned away from the remainder of the pool and amplified as described in the SELEX method. The facilitating nucleic acid can be partitioned alone or along with its associated desirable product. The amplified nucleic acids are enriched for the nucleic acids which are amplified nucleic acids are then products. The amplified nucleic acids are then recoupled to the first reactant, recontacted with the free reactants, and the iterative cycling of the selection/amplification steps of the SELEX process are incorporated to synthesize, select and identify desirable products. The selected nucleic acids ultimately produce enough of the desirable product so that the structure can be determined.

II. THE REACTION

A. The Nucleic Acid

Parallel SELEX depends on the ability of a nucleic acid to mediate product formation. The method requires the initial preparation of a nucleic acid test mixture. In general, the rationale and methods for preparing the nucleic acid test mixture are as outlined in the SELEX patent applications described earlier which are herein incorporated by reference. Briefly, a nucleic acid test mixture of differing sequences is prepared. Each nucleic acid in the test mixture generally includes regions of fixed sequences (i.e., each of the members of the test mixture contains the same sequences in the same location) and regions of randomized sequences. The fixed sequence regions are selected either: (a) to assist in the amplification steps described in detail in the SELEX patents, (b) to mimic a sequence known to mediate a reaction, or (c) to enhance the concentration of nucleic acids of a given structural arrangement in the test mixture. The randomized sequences can be totally randomized (i.e., the probability of finding a base at any position being one in four) or only partially randomized (e.g., the probability of finding a base at any location can be selected at any level between 0 and 100 percent). The nucleic acids found in the nucleic acid test mixture will include those capable of proper folding in order to specifically mediate various chemical reactions.

The nucleic acid test mixture can be modified in various ways to enhance the probability of the nucleic acids having facilitating properties. The modifications contemplated by this invention are any modifications which introduce other chemical groups that have the correct charge, polarizability, hydrogen bonding, electrostatic interaction, or fluxionality and overall can adopt the shape needed to stabilize the reaction transition state and facilitate specific chemical reactions, without limitation. The modifications that may enhance the active site of the nucleic acid include hydrophilic moieties, hydrophobic moieties, metal atoms in various oxidation states, rigid structures, functional groups found in protein enzyme active sites such as imidazoles, primary alcohols, carboxylates, guanidinium groups, amino groups, thiols and the like. Additionally, organometallic and inorganic metal catalysts can be incorporated as the other chemical group of the nucleic acid, as can redox reactants.

The individual components of a nucleic acid test mixture can be modified in various ways. Suitable modifications include, but are not limited to, modifications on every residue of the nucleic acid, on random residues, on all pyrimidines or purines, or all specific bases (i.e., G, C, A, T or U), or one modification per nucleic acid. It is also recognized that certain molecules (e.g., metal catalysts and the like) can be in solution, not attached to the nucleic acid, and be useful in mediating the reaction in concert with the mediating action of the nucleic acid. It is believed that as long as the nucleic acid coupled to the first chemical reactant is in some way associated with mediating the chemical reaction that the method and products fall within the scope of this invention. It is also recognized that modification is not a prerequisite for facilitating activity of the nucleic acids of the invention.

i. Modifying Nucleotides with Other Chemical Groups

The nucleotides can be modified in any number of ways, including modifications of the ribose and/or phosphate and/or base positions. Certain modifications are described in copending U.S. patent applications No. 08/117,991 entitled "High Affinity Nucleic Acid Ligands Containing Modified Nucleotides and Ser. No. 08/076,735 entitled "Method for Palladium Catalyzed Carbon-Carbon Coupling and Products," now U.S. Pat. No. 5,478,149 which are herein incorporated by reference. In one embodiment, modifications are those wherein another chemical group is attached to the 5-position of a pyrimidine, the 8-position of a purine, or the 2' position of a sugar. There is no limitation on the type of other chemical group that can be incorporated on the individual nucleotides. In the preferred embodiments, the resulting modified nucleotide is amplifiable or can be modified subsequent to the amplification steps.

As an example, which is not meant to limit the invention in any way, one can envision a biomimetic facilitating nucleic acid. One choice for modification of the nucleic acids includes modification which would make certain bases appear more like proteins in their chemical and physical properties. Certain modifications of pyrimidine and purine nucleotide bases can be made to make the nucleic acid appear to have "side chains" similar to the amino acid side chains of proteins. Several synthetic methods are available to attach other chemical groups, in this case amino acid derivatives, to the 5-position of a pyrimidine or the 8-position of a purine. Methods for modifying pyrimidines at the 5-position have been described in U.S. patent application Ser. No. 08/076,735 (now U.S. Pat. No. 5,428,149) as well as other published procedures. Numerous published procedures are known for modifying nucleic acids including, but not limited to the following (Limbach, P. A., et al., 1994. *Nucleic Acids Res.* 22:2183–2196 and references cited therein; Hayakawa H. et al., 1985. *Tetrahedron* 41:1675-83; Crouch G. J. et al., 1994. *Nucleosides & Nucleotides* 13:939–44; Scheit K. H., 1966. *Chem. Ber.* 98:3884; Bergstrom and Ruth, 1976. *J. Am. Chem. Soc.* 98: 1587–89; Bergstrom and Ogawa, 1978. *J. Am. Chem. Soc.* 100:8106–12; Ruth and Bergstrom, 1978. *J. Org. Chem.* 43:2870; Bergstrom D. E. et al., 1981. *J. Org. Chem.* 46:1432–41; Bergstrom D. E. 1982. *Nucleosides & Nucleotides* 1:1–34; Crisp and Flynn, 1990. *Tetrahedron Lett.* 31:1347–50; Hobbs F. W. Jr. 1989. *J. Org. Chem.* 54:3420–22; Hirota K. et al., 1993. *Synthesis* 213–5; Nagamachi T. et al., 1974. *J. Med. Chem.* 17:403–6; Barton D. H. R et al., 1979. *Tetrahedron Lett.* 3:279–80; Hirota K. et al., 1992. *J. Org. Chem.* 57:5268; Mamos P. et al., 1992. *Tetrahedron Lett.* 33:2413–16; Sessler J. L. et al., 1993. *J. Am. Chem. Soc.* 115:10418–19.; Long R. A. et al., 1967. *J. Org. Chem.* 32:2751–56; Prakash T. P. et al., 1993. *Tetrahedron* 49:4035; Janokowski A. J. et al., 1989. *Nucleosides & Nucleotides* 8:339; Kumar and Buncel, 1984. *J. Inorg. Biochem.* 22:11–20; Moffatt J. G. 1979. in *Nucleoside Analogues*, eds. R. T. Walker, E. De Clercq, F. Eckstein pp. 71–163 New York: Plenum Press; Townsend L. B. 1988. *Chemistry of Nucleosides and Nucleotides* pp. 59–67 New York: Plenum Press; Verheyden J. P. H. et al., 1971. *J. Org. Chem.* 36:250–54; Wagner D., et al., 1972. *J. Org. Chem.* 37:1876–78; Sproat and Lamond 1991. In *Oligonucleotides and Analogues A Practical Approach*, ed. F. Eckstein pp.49–86. New York: Oxford University Press; Lesnik E. A. et al., 1993. *Biochemistry* 32:7832–38; Sproat B. S. et al., 1991. *Nucleic Acids Res.* 19:733–38; Matsuda A et al., 1991. *J. Med. Chem.* 34:234–39; Schmit C. 1994. *Synlett* 238–40; Imazawa and Eckstein, 1979. *J. Org. Chem.* 44:2039–4; Schmit C. 1994. *Synlett* 241–42; McCombie and Metz, 1987. *Tetrahedron Lett.* 28:383–6; Imazawa M., et al., 1975. *Chem. Pharm. Bull.* 23:604–10; Divakar K. J. et al., 1990. *J. Chem. Soc., Perkin Trans.* 1 969–74; Marriott J. H. et al., 1991 *Carbohydrate Res.* 216:257–69; Divakar and Reese, 1982. *J. Chem Soc., Perkin Trans.* 1625–28; Marriott J. H. et al., 1990. *Tetrahedron Lett.* 31:7485–88)

The above-described amino acid-modified nucleotides can be substituted for the native nucleotides and incorporated into the sequences of the nucleic acid test mixture. Nucleotides modified with other chemical groups in place of the above-described amino acids are also contemplated by this invention. Oftentimes, a working assumption can be made about which modified nucleotides would be most desirable for addition to the nucleic acid test mixture. For example, if the reaction which is intended to be mediated is an aldol condensation, guided by the structure of Class I Aldolases, the needed other chemical group could be an amino acid derivative that contains a primary amino group to form an imine with the carbonyl substrate and another basic group to facilitate formation of the enamine that serves as the nucleophile in the reaction.

ii. Modifying the Nucleic Acid with Organometallic Groups

Another modification to the nucleic acid test mixture contemplated by this invention is incorporating an organometallic reagent into the sequences that make up the nucleic acid test mixture. Use of organometallic catalysts in the synthesis of complicated organic structures has revolutionized organic syntheses. An organometallic catalyst is any metal and organic ligand sphere capable of mediating a reaction. The ligands that can make up the coordination sphere are known to those skilled in the art, and include pyridine ligands, phosphine ligands, oxime ligands, porphyrins, isocyanates, cyanates, carboxylates, thiols, carbon monoxide, alkenes, ethers and the like. Useful metals include nickel, rhodium, cobalt, palladium, zirconium, aluminum, iron, manganese, titanium, ruthenium, molybdenum and boron. For example, pyridinium nickel complexes are known to catalyze urea hydrolysis; rhodium acetate catalysts facilitate cyclopropanation; cobalt complexes catalyze cyclotrimerization and [3+2] cycloaddition; palladium catalyzes hydrogenation and [3+2] cycloaddition; ruthenium and molybdenum complexes catalyze olefin metathesis. Taken together these reactions can prepare 3, 4, 5, 6 and 7 membered rings, all of which are known to be useful in the structure of many medicinal compounds. Larger rings may be prepared by π-allyl palladium catalysis. Formation of chiral centers is crucial to the synthesis of many biologically active compounds and in many cases the wrong enantiomer can have deleterious pharmacological effects. In trimerization, asymmetric hydrogenation to form single enantiomers has been accomplished by palladium and zirconium complexes.

In this embodiment, several options are available to connect the organometallic complex to the oligonucleotide. The organometallic complex can be attached directly to the nucleotide base, such as at the 5-position of a pyrimidine. The modified oligonucleotide should amplify with good integrity.

In some cases, the linkage between the nucleic acid and the organometallic complex should be clearable, leaving the oligonucleotide intact. Examples of cleavable linkages include, but are not limited to, photochemically labile linkers, disulfides and carbonates. These linkage chemistries are well known to those of ordinary skill in the art and could be used to attach the organometallic complex to the 5' or 3' end of a nucleic acid or the 5-position of pyrimidine residues in the nucleic acid.

Another option would be to use a cassette oligonucleotide that may be synthesized to include an organometallic complex. The cassette oligonucleotide embodiment would include a fixed nucleic acid sequence having an organometallic complex associated with it which could be ligated onto the nucleic acid at the start of each round of selection. Each member of the nucleic acid test mixture would have an identical fixed region complementary to the fixed sequences of the cassette. This cassette oligonucleotide may obviate the need for other conjugation methods.

It may also be desirable to embed the organometallic catalyst within an oligonucleotide. For some of these embodiments, the modification can take place after each round of amplification. In the case of embedding the organometallic complex within the oligonucleotide, more than one clearable bond may be desirable and the chemistry of each cleavable bond will need to be unique. The bipyridine ligand is used as an example in the scheme shown below.

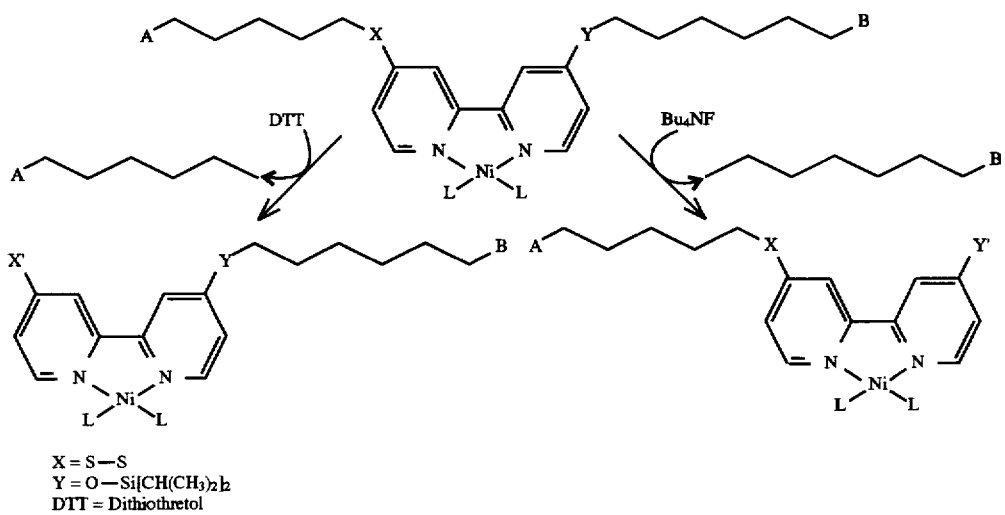

X = S—S
Y = O—Si[CH(CH₃)₂]₂
DTT = Dithiothretol

Because the oligonucleotide components labeled A and B may be chemoselectively cleaved from the support their sequences may be determined independently. In addition, A and B may be comprised of relatively short sequences that would be readily synthesized by chemical methods. For some organometallic complexes it will be required that the metal be incorporated subsequent to synthesis or transcription. In these cases the chelating ligands that bind the metal would be attached to the oligonucleotide as discussed above and the metal introduced after nucleic acid synthesis or amplification by ligand exchange reactions.

As can be seen from the examples provided above, there are numerous ways to modify the nucleic acid to enable it to mediate chemical reactions, such as bond formation and bond cleavage. All modifications of the nucleic acid are contemplated by this invention.

B. The Reactants

In its broadest sense, the term reactants refers to any chemical entity that is compatible with the thermal and chemical stability of nucleic acids which can be involved in a bond forming or bond cleaving reaction. This invention should not be limited by the type of reactant. The following classes of small organic molecules are intended to be non-limiting examples of potential reactants: alkenes, alkynes, alcohols, aldehydes, ketones, esters, carboxylic acids, aromatic carbocycles, heterocycles, dienes, thiols, sulfides, disulfides, epoxides, ethers and halogenated compounds. The reactants preferably have a molecular weight in the range of 2 to 1000, most preferably in the range of 26 to 500. Where the desired products are larger molecules, the reactants would also be larger, such as with peptides, proteins and polymers. The reactants can contain more than one of the listed functionalities and can contain chiral centers. In general, the term reactants represents a class of chemical reactants defined by its chemically reactive unit (e.g., diene, ester, etc.). As an example, the chemical reactant can be a class of reactants which could include 1 to $10^n$ different members of the class. The reactants chosen for any given reaction may also include several classes of reactants.

At some level in the process of determining suitable reactants for the Parallel SELEX process, a target must be identified and the mode of action by which a desirable product would act on such target must be determined. Once that determination is made, a class of products thought likely to have the desirable properties can be selected. Suitable reactants that are likely to produce the desired class of products can then be selected and incorporated into the Parallel SELEX process.

The selection of reactants can be determined randomly. However, preferably the choice of reactants can be based upon a number of criteria including, but not limited to, selecting reactants based on the desired class of products, which can be determined by initial structural assumptions based on similarity to known compounds having a desired characteristic, other known ligands, computer modeling simulations, NMR and X-ray data/structure, enzymatic and chemical footprinting experiments. Once a product class is identified, the reactants are selected to maximize the variability that can be obtained. Often, retrosynthesis procedures are employed to select possible reactants. Multiple classes of reactants can be used simultaneously.

For the purposes of this invention, the reactant which is coupled to the nucleic acid will be termed the first reactant or coupled reactant. Typically, the first reactant will be contacted with at least one free reactant under conditions favorable for facilitated bond formation, and the resulting product will be assayed to determine if it has a predetermined desirable characteristic. It is envisioned that a first reactant can chemically react with more than one other reactant (i.e., second, third, forth, etc. reactants) to form a product. It is also envisioned that more than one type of chemical reaction can be taking place simultaneously. It is also contemplated that multiple reactions may be taking place simultaneously, possibly using multiple nucleic acids to facilitate different portions of the product formation. Ideally, reactants are selected so that, depending on the ability of the facilitating nucleic acids to specifically generate products, a product library is created.

C. Coupling the Reactant to the Nucleic Acid

Parallel SELEX requires that the first reactant be coupled to the nucleic acid having facilitating properties which is present in the nucleic acid test mixture. The first reactant is coupled to the nucleic acid either covalently or non-covalently. The coupling can theoretically be anywhere on the nucleic acid. However, for practical purposes, the coupling usually takes place on the 5' or 3' ends of the nucleic acid. Typically, the coupling is through a ligation reaction, but any known coupling reaction is acceptable. The coupling can be direct, as could be done with a 5' GMPS, a 3' dideoxy with terminal transferase, or the like.

The coupling between the nucleic acid and reactant may also include a linker group. Such a linker group may allow the nucleic acid to fold in a more favorable conformation so that it can better interact with the reactants to mediate the bond formation reaction. The linker group may allow the first reactant to explore the entire surface and catalytic pockets of the folded nucleic acid.

The linker group can be any suitable spacer moiety. The linker group should contain a sufficient length, preferably made up of polymeric units, to allow for a flexible tether that would enable the various reactants access to the entire surface and binding pockets of the folded nucleic acid. The optimal size of the linker is dependent on the size of the nucleic acid. In general, the size of the linker group should be between 10 and 1000 Å, preferably between 50 and 300 Å. The linker group can be varied in the nucleic acid-reactant test mixture to select optimum length for a desired reaction. The linker group should also be easily solvated under the reaction conditions. Suitable linker groups are exemplified by PEG, poly vinyl alcohol, polyacrylates and polypeptides.

The linkage between the linker group and the nucleic acid preferably is cleavable, leaving the nucleic acid intact. Examples of suitable cleavable linkages include, but are not limited to, photochemically labile linkers, disulfides, and carbonates. The linkage can also be cleavable with enzymes, such as DNAse and proteinases.

Additionally, the linkage can be by the Splint Blended SELEX method described in U.S. Ser. No. 08/234,997, filed Apr. 28, 1994, entitled Systematic Evolution of Ligands by Exponential Enrichment; Blended SELEX which is herein incorporated by reference.

D. Product Formation

A chemical reaction occurs when a first reactant and at least a second reactant interact and form a product or when a first reactant is cleaved in someway that is facilitated by its associated nucleic acid. Any number of chemical reactions are compatible with the Parallel SELEX method. The only requirement is that the reaction be mediated by the nucleic acid coupled to the first reactant. Preferably, the mediation by the nucleic acid is specific for the reactants and desired product, however, that may not always be the case. The chemical reactions include both bond formation and bond cleavage reactions. Various bond formation reactions are contemplated by this invention and by way of example include condensation/hydrolysis reactions, cycloaddition reactions such as the Diels-Alder and Ene reaction, conjugate addition to $\alpha,\beta$-unsaturated compounds, Aldol condensations, glycosylation of peptides, sugars and lipids. Additionally, when the nucleic acids in the test mixture are modified to include incorporating an organometallic catalyst into the nucleic acid, other reactions, including, but not limited to, cyclopropanation, hydrogenation, cyclotrimerization of alkynes, [3+2] and [4+1] cycloaddition of unsaturated molecules, and olefin metathesis may occur, all of which could form asymmetric molecules. This invention contemplates use of these reactions alone or together in any combination. This invention further contemplates successive reactions wherein a first product can be made with two or more reactants and then that product can become a "reactant" with other free reactants to form a second product, etc.

Bond cleavage reactions are also included in this invention. Bond cleavage reaction has several embodiments, including, but not limited to, cleavage of the first reactant to form a product that interacts with a target, cleavage of the first reactant so that it is now able to better react with a second reactant to form a new product, etc.

The invention also includes embodiments wherein the products formed by the method of the invention are attached to other molecules, including but not limited to, labels, antibodies, other small molecules, etc.

The reaction(s) can take place under a variety of conditions known to one of ordinary skill in the art, which are consistent with the stability requirements of nucleic acids. The reaction can take place in any buffered or non-buffered aqueous solvent, such as water, Tris, HEPES, etc. or in an organic solvent system with appropriate alkyl ammonium or similar counter ions, such as methanol/water, DMSO, DMF/water, with triethylammonium salt. The temperature range is generally $-10°$ C. to $100°$ C., preferably $10°$ C. to $50°$ C. The concentration of the randomized nucleic acid-reactant test mixture is generally in the range of 1 pM to 10 mM, preferably 1 to 100 µM, and the concentration of the second reactant is generally in the range of 1 µM to 10 µM, preferably 10 µM to 10 mM.

E. Partitioning Products having Predetermined Desirable Characteristics

Once a chemical reaction has taken place, one must screen the product library for products having predetermined desirable characteristics. As described earlier, predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. The conditions under which the products are screened are not limited to the conditions for product formation described in section D above. Screening conditions are known to one of ordinary skill in the art.

Products having predetermined desirable characteristics can be partitioned away from the rest of the product library while still attached to the nucleic acid which facilitated their formation by various methods known to one of ordinary skill in the art. The key is to partition the desirable products away from the entire product library without chemical degradation of the attached nucleic acid such that the nucleic acids are amplifiable. The nucleic acid can then be amplified, either still attached to the desirable product or after separation from the desirable product, as taught in the basic SELEX method.

In the most preferred embodiment, the desirable product acts on the target without any interaction between the nucleic acid attached to the desirable product and the target. The nucleic acid facilitates the reaction between its attached reactant and a free reactant yielding the desirable product, and also is amplifiable to that the desirable product can be subsequently reproduced and ultimately identified from the vast product library. However, it is not envisioned in this preferred embodiment that the nucleic acid interacts directly with the target.

The nucleic acid can be modified prior to contact with the target to ensure that it does not interact with the target. The modification can take place several ways, including making the nucleic acid double stranded so that it is less capable of interacting with the target. In a somewhat less preferred embodiment, the nucleic acid can act on the target, either independently or in concert with the desirable product whose synthesis it facilitated. In this embodiment, the ultimate product could be a combination of the product with the associated nucleic acid.

In one embodiment, the product binds to the target and the bound nucleic acid-product-target complex can be partitioned from unbound products by a number of methods. The methods include nitrocellulose filter binding, column chromatography, filtration, affinity chromatography, centrifugation, and other well known methods. Briefly, the product library is subjected to the partitioning method, such as a column onto which the target is bound. All nucleic acids which have not formed products or those associated with undesirable products will pass through the column or can be removed by Counter-SELEX. Desirable products are bound to the column and can be eluted by changing the conditions of the column (e.g., salt, etc.) or the nucleic acid associated with the desirable product can be cleaved from the product and eluted directly.

Additionally, products which react with a target can be separated from those products that do not react with the target. In one example, a product which covalently attaches to the target (such as a suicide inhibitor) can be washed under very stringent conditions. The resulting product-target complex can then be treated with proteinase, DNAse or other suitable reagent to cleave a linker and liberate the nucleic acids which are associated with the desirable products. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

As described earlier, the SELEX process can include other embodiments which could be incorporated for the successful partitioning of desirable products, including but not limited Photo-SELEX, Counter-SELEX, etc.

In one embodiment, before the partitioning step, the nucleic acid is treated in such a way that it is less likely to interact with the target. As an example, the nucleic acid can be made double stranded before partitioning. In another embodiment, prior to coupling the reactant to the nucleic acid, the nucleic acid test mixture can be partitioned via Counter SELEX to eliminate nucleic acids which act directly on the target.

F. Amplification

Amplification of the nucleic acid that directs the synthesis of the product having desirable characteristics is done as described in the basic SELEX method using methods known to one of ordinary skill in the art. If necessary or desirable, any modification or other added feature (such as the linker group) may be removed prior to amplification. Polymerase chain reaction (PCR) is an exemplary method for amplifying nucleic acids. Descriptions of PCR methods are found, for example in Saiki et al., 1985. *Science* 230:1350–1354; Saiki et al., 1986. *Nature* 324:163–166; Scharf et al., 1986. *Science* 233:1076–1078; Innis et al., 1988. *Proc. Natl. Acad. Sci.* 85:9436–9440; and in U.S. Pat. No. 4,683,195 (Mullis et al.) and U.S. Pat. No. 4,683,202 (Mullis et al.). In its basic form, PCR amplification involves repeated cycles of replication of a desired single-stranded DNA, or cDNA copy of an RNA, employing specific oligonucleotide primers complementary to the 3' and 5' ends of the ssDNA, primer extension with a DNA polymerase, and DNA denaturation. Products generated by extension from one primer serve as templates for extension from the other primer. Other known amplification methods are contemplated by this invention.

The amplified nucleic acid then is subjected to any required post-amplification modification, recoupled to the first reactant and the process continues as described above. The process is repeated as many times as necessary to enrich for nucleic acids having the appropriate facilitating activity and/or until desirable products having maximal desirable characteristics are obtained. It is entirely possible that one round of Parallel SELEX is all that is required to obtain a product having desirable characteristics. The endpoint can be determined by many methods which would be understood by one of ordinary skill in the art, including binding curves, inhibition determined by $IC_{50}$ values, rates of inactivation, toxicity profiles, bioavailability, pharmacokinetics, etc.

G. Analyzing Desirable Products

After amplifying the nucleic acid facilitator and producing sufficient quantities of the desirable product, the structure of one or a series of desirable products can be solved by conventional spectroscopic methods known to one of ordinary skill in the art. In order to do this, the initial reaction conditions must be suitably replicated. The first reactant should be recoupled to the nucleic acid facilitator, the resulting nucleic acid-reactant mixed with the pool of second reactants and the resulting desirable product formed and isolated. The assumption that enables this process to be most effective is that the nucleic acid will specifically facilitate the individual reactions or at least a relatively small number of reactions, including the desired reaction. The conventional spectroscopic methods include, but are not limited to, NMR spectroscopy, mass spectroscopy, HPLC spectroscopy, circular dichroism, polarimetry, and X-ray crystallography. Once the structure of the desirable product has been identified, it can be produced in large quantities either by standard chemical synthesis procedures or by the procedures outlined herein for production using a facilitating nucleic acid.

III. Generic Examples

The following generic examples are included to additionally describe the Parallel SELEX method. The most basic scheme for the Parallel SELEX method is outlined in FIG. 1. The following examples describe in more detail a small sampling of reactions that are contemplated by the invention. It is intended that these examples are provided for illustration purposes only and are not meant to limit the invention in any way.

a. A Diels-Alder Reaction

The following discussion describes how RNA facilitators and a cyclohexene small molecule product which will bind to a generic target may be coevolved utilizing the Diels-Alder reaction depicted in FIG. 2A–2D. Another version of this Parallel SELEX example could employ DNA and in some cases DNA may be preferable to RNA.

The starting RNA (A of FIG. 2A) would contain 3' and 5' fixed regions to allow for transcription and a ligation site for conjugation to a PEG spacer which is in turn connected to a first reactant dienophile. The starting RNA (A) will have a randomized region consisting of approximately 4N different sequences, wherein N is the number of nucleotides in the RNA sequence; the exact number will depend on the length of the random region and the scale of RNA synthesis used to make it. The PEG spacer would contain a sufficient number of polymeric units to allow for a flexible tether that would enable the first reactant dienophile access to the entire surface and binding pockets of the folded RNA (C and D of FIG. 2A). The starting RNA (A) which is coupled to the first reactant is depicted as a linear structure for the sake of clarity. The actual RNA structures will consist of different folded motifs as represented by C and D.

In this example, Step 1 will include a pool of 10 second reactant diene substrates labeled $B_{1-10}$ where the groups $R^1$, $R^2$ and $R^3$ are not hydrogen. There is no reason that the pool could not be expanded to include second reactant dienes where one or all of the groups $R^1$, $R^2$ and $R^3$ are hydrogen. This would only result in a fewer number of stereocenters being formed. Structures C and D represent the two possibilities for approach of the first reactant dienophile. Each regioisomer will have four possible stereoisomers that may form and if all are produced, 11 compounds will be transformed into 80. (FIG. 2B) Diagramatic structural elements a and B represent theoretical bulges in the RNA that can interact with the second reactant diene or first reactant dienophile to determine the orientation of the second reactant diene and the approach of the second reactant diene at the transition state. For example, for $E_{1-10}$ if $R^3$ is smaller than $R^2$ the preferred orientation of the diene would favor formation of E/E* and F/F* in contrast to G/G* and H/H* because of steric interference between the RNA features B and dienophile group $R^2$. For approach C, enantiomers E/E* and F/F* will be formed. Attractive interaction such as H-bonding between the dienophile carboxylate oxygen and the RNA region labeled a would facilitate formation of the endo products. Attractive forces between $R^1$ and the RNA surface labeled B could also favor endo attack. In contrast, the RNA structural features a and b could have repulsive interactions with the carboxylate and $R^1$ of the dienophile which would result in formation of the exo products. Note that the relationship between the pairs E/E* and F/F* is diastereomeric so they will have different physical properties even for identical substituents $R^1$, $R^2$ and $R^3$. For approach D, enantiomers G/G* and H/H* will be formed and the relationship between the pairs G/G* and H/H* is diastereomeric. However, because the oligonucleotide has inherent chirality, the RNA facilitative site will have an energetically different, diastereomeric interaction with the transition state of the enantiomeric pairs which could allow for high enantioselectivity even if the energy difference is small ($\Delta\Delta G\ddagger 3-4$ kcal/mol).

Figure 2A:
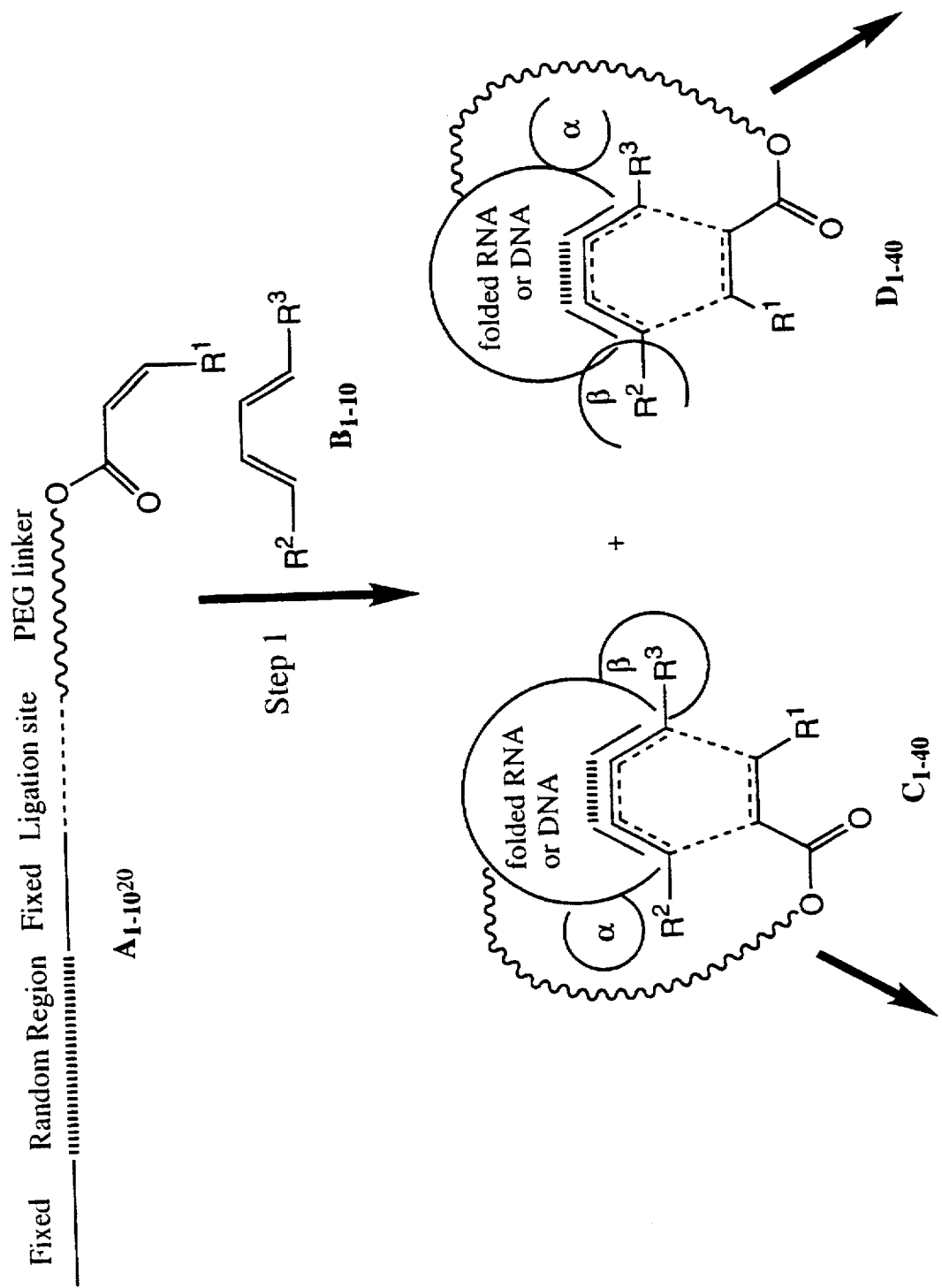
FIGS. 2A–2D depict a schematic representation of the Parallel SELEX process wherein a facilitating nucleic acid mediates a generic Diels-Alder reaction between a diene and a dienophile.
Figure 2B:
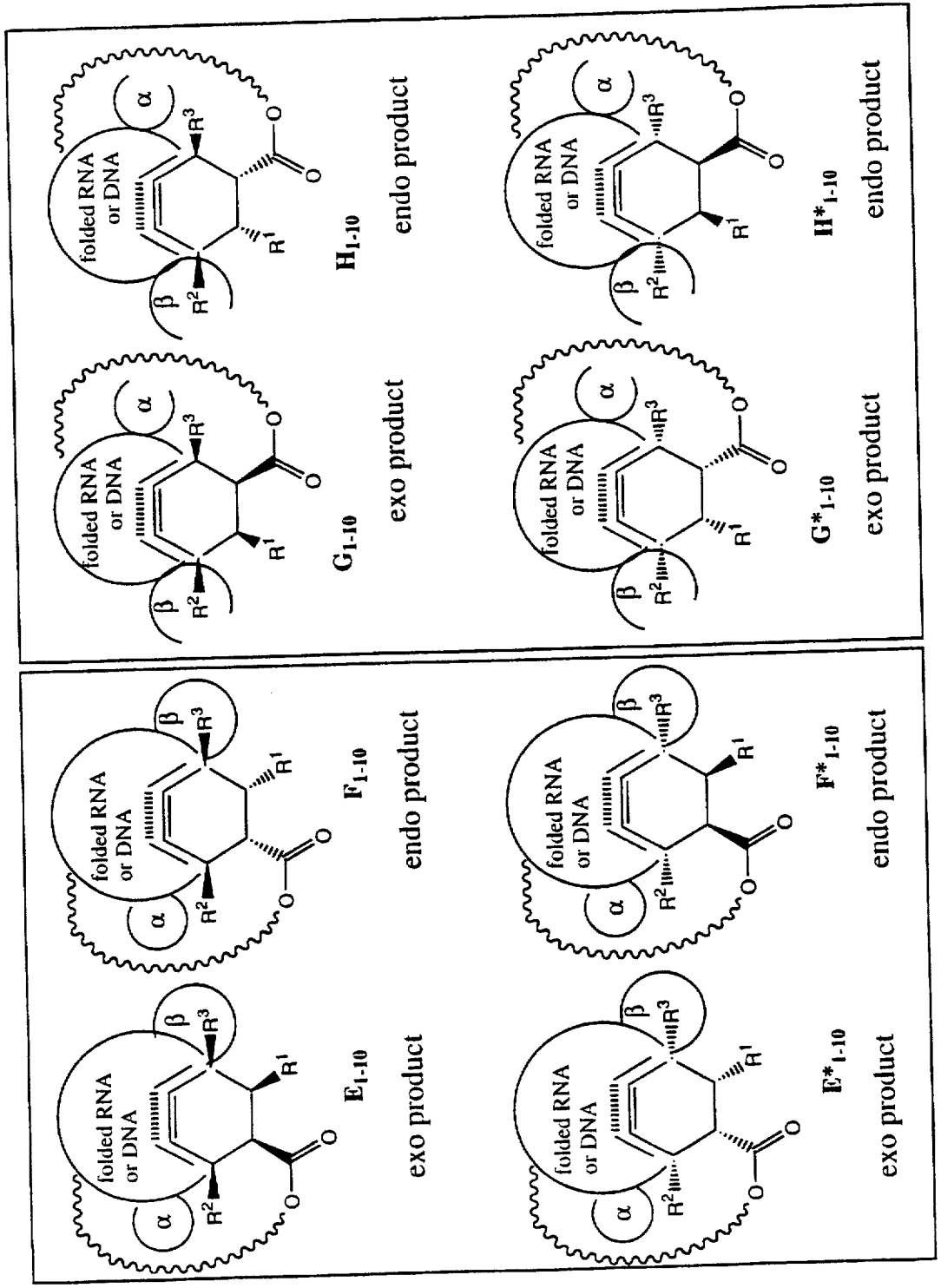
Figure 2C:
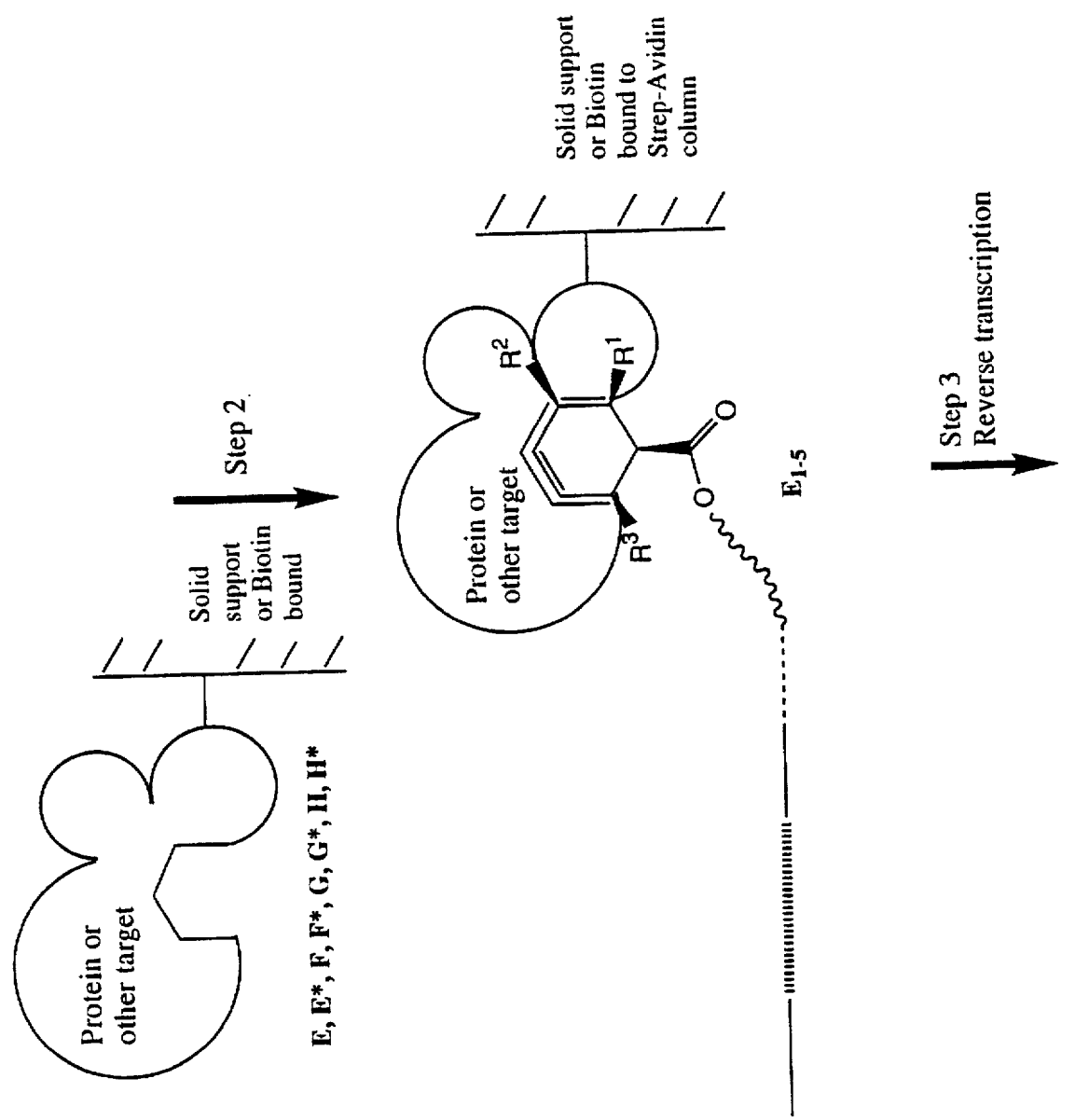

The selection of the cyclohexene desirable products is described by Step 2 (FIG. 2C). If the target is a protein and the desirable product is selected for binding to the target, step 2 could be performed in target protein excess during initial rounds and the protein concentration would then be decreased as enrichment of the cyclohexene desirable product increases. Examples of target proteins could include enzymes, hormones, cell receptors, cell adhesion molecules etc. In a competition assay the highest affinity desirable products will be bound. This could result initially in the selection of entire groups such as E/E* and F/F*. For this example it is assumed that one enantiomer set is selected, say E, because it binds more tightly to the target protein, and for the sake of an example only 5 of the 10 possible structures are of comparable affinity $E_{1-5}$ depicts the five "winners" which bound to the protein. (It will be noted that there is no a priori reason to believe that desirable products could not be obtained that were derived from each of the diastereomers.)

Figure 2D:
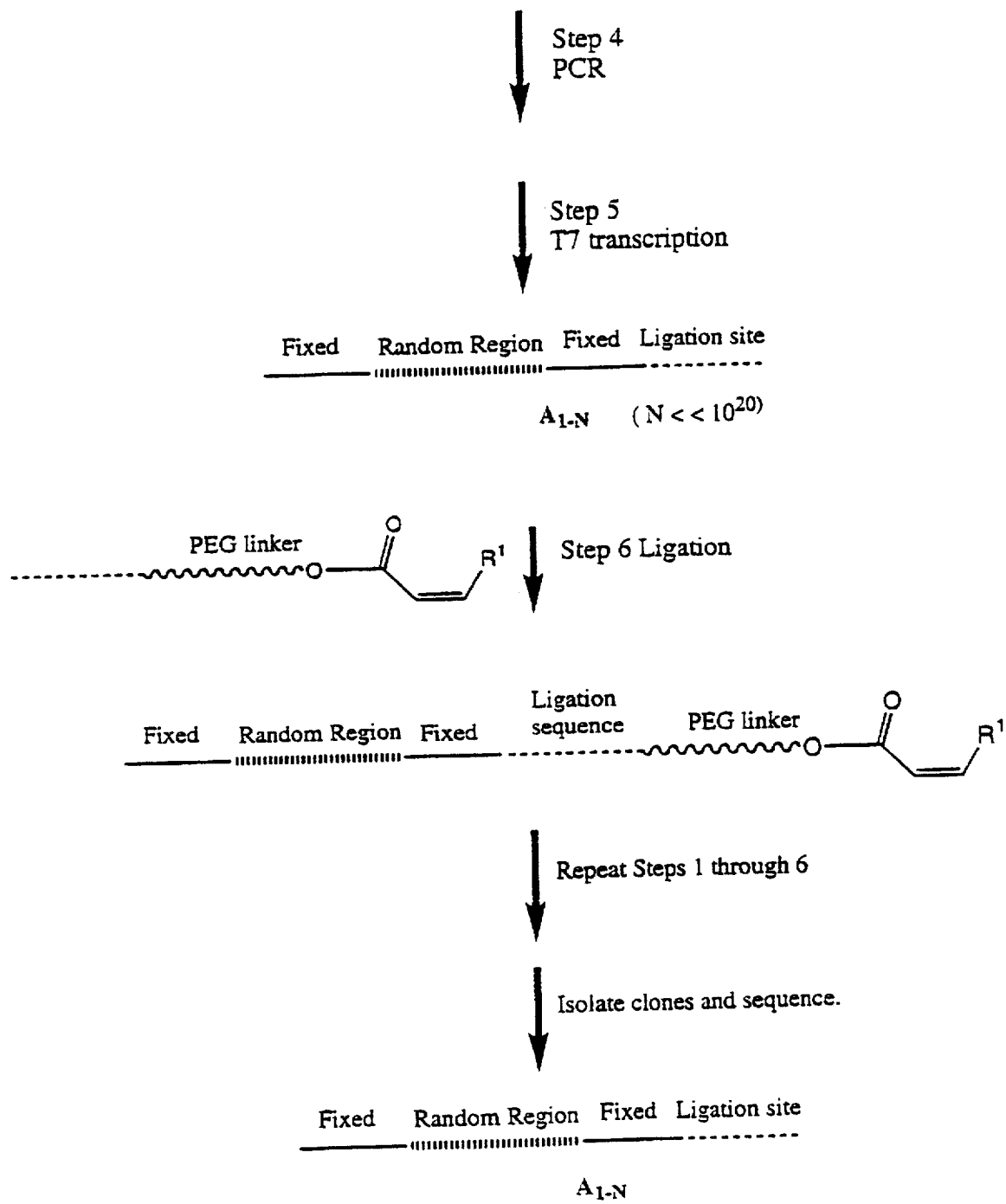

The selected desirable products and their attached, coevolved RNA facilitators are partitioned from the undesirable products and the RNA facilitators are amplified by the standard SELEX procedures of Steps 3 through 5 (FIGS. 2C and 2D). After Step 5, the RNAs have been enriched for facilitating activity that specifically forms the E group of compounds. The RNA structure obtained after step 5 when folded up is the active catalyst for the formation of the cyclohexene products denoted by E in FIG. 2C. There could be more than 5 RNAs at this point. To perform subsequent rounds of SELEX would require Step 6 in which the initial PEG spacer with first reactant dienophile is ligated to the new enriched pool of RNAs. Repeating Steps 1 through 6 could further enrich for the facilitating activity of the RNA obtained after Step 5. Additionally, the binding affinity of the cyclohexene desirable products could reach a maximum. Assuming that the RNA pool is now non-random, by cloning and sequencing the different RNAs the individual RNA molecules could be tested for the facilitating activity. Treating these RNA molecules with the same first and second reactant dienophile and dienes would by necessity result in the formation of the coevolved cyclohexene desirable product. After producing sufficient quantities of the RNA facilitator, the structure of one or a series of cyclohexene desirable products is solved by conventional spectroscopic methods.

The example given above was for a single first reactant dienophile treated with a pool of 10 second reactant dienes. The number of first reactant dienophiles to be included in the coevolution process may be expanded by simply attaching a number of different first reactant dienophiles to the ligation sequence. After coevolution, cloning and sequencing the individual RNA facilitators would then be treated with the mixture of first and second reactant dienes and dienophiles so that the individual desirable product formed by the facilitating RNA would be made in sufficient quantity to allow for spectroscopic structural identification. Since in the Parallel SELEX example shown above the first reactant dienophile is attached to the RNA it is assumed that the facilitating RNA will be specific for reaction of the attached first reactant dienophile as opposed to those attached to other RNAs. It may turn out that treating a single facilitating RNA with a pool of first and second reactant dienes and dienophiles will result in a very specific reaction with respect to the second reactant diene, because this was what was selected for, but poor selectivity for the first reactant dienophile, since this is attached during the selection.

Figure 3:
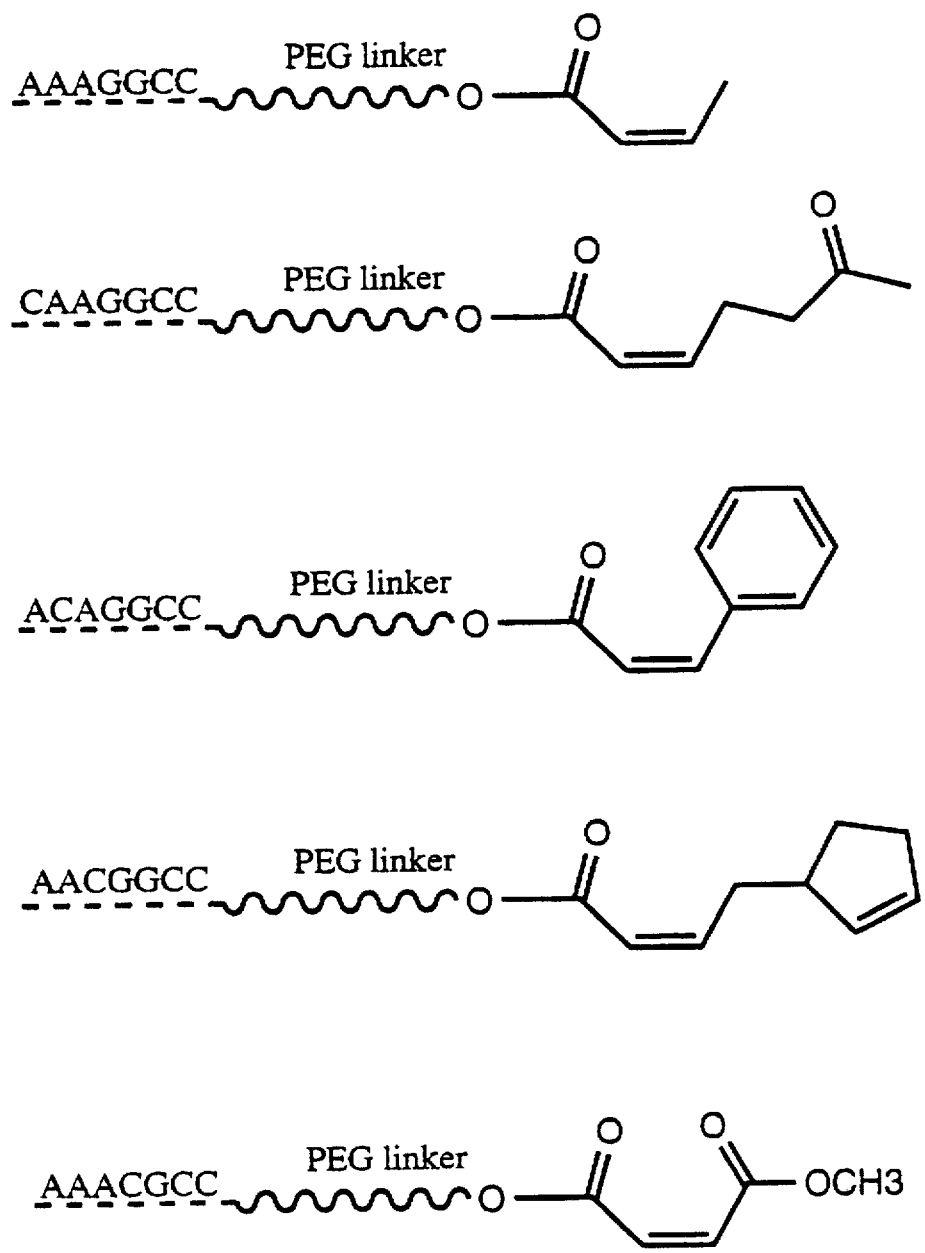
FIG. 3 depicts how ligation sequences may be used to expand the array of second reactant molecules in Parallel SELEX. Five of the possible 16,384 possibilities consistent with FIG. 2 are shown.

On the other hand, if both first and second reactants are varied, specificity for both reactants could be obtained. An improved embodiment would be to use the ligation sequence to code for the first reactant dienophile that is attached to a particular nucleic acid as shown in FIG. 3, and thus allowing for the matrix to be expanded. Using this approach, on cloning and sequencing of the individual facilitating RNAs the sequence of the ligation site would indicate the first reactant dienophile that was attached to it through the PEG linker. In this way only the first reactant dienophile corresponding to the particular facilitating RNA would be used for the final preparation of the evolved desirable product. It should be noted that there is no reason why a complementary experiment to the one proposed in FIGS. 2A–2D could not be employed where a single first reactant diene is attached to the RNA ligation sequence and a pool of second reactant dienophiles introduced into Step 1. It is also possible to use multiple first reactants and one second reactant.

The Diels-Alder is only one of a number of very powerful asymmetric bond forming reactions.

b. An Aldol Reaction

Figure 4A:
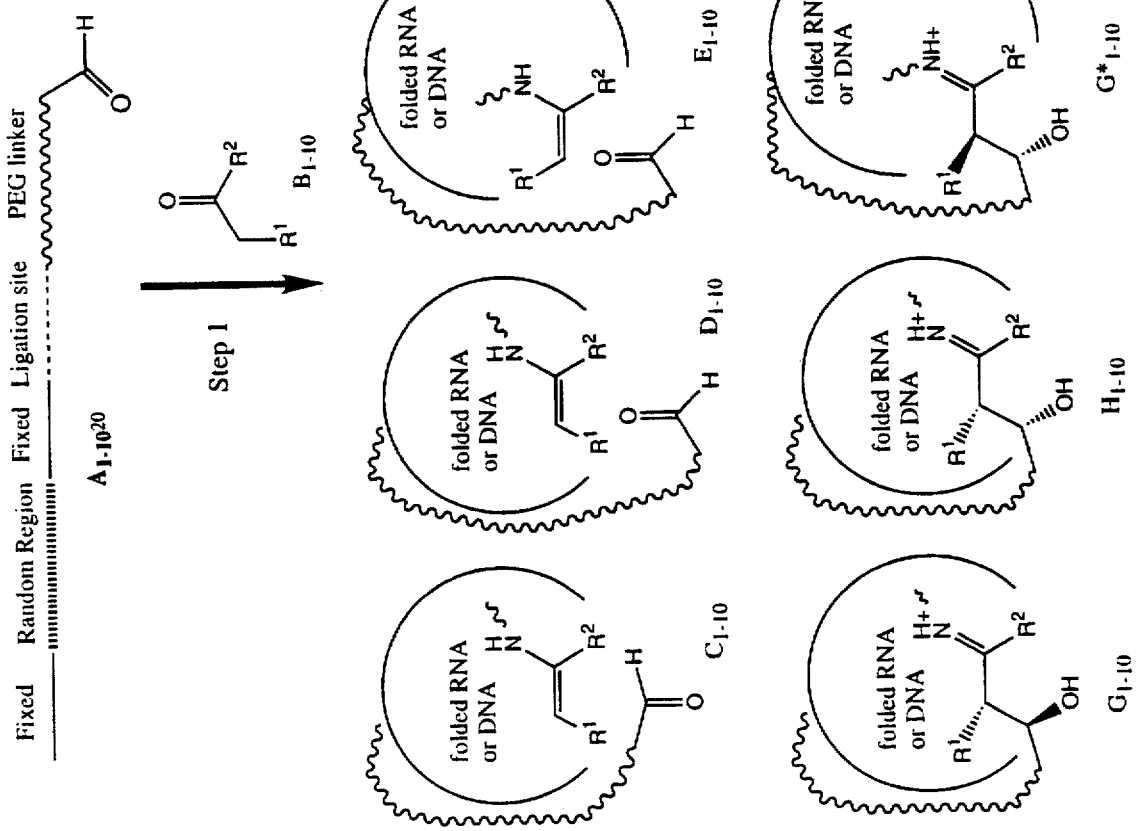
Figure 4C:
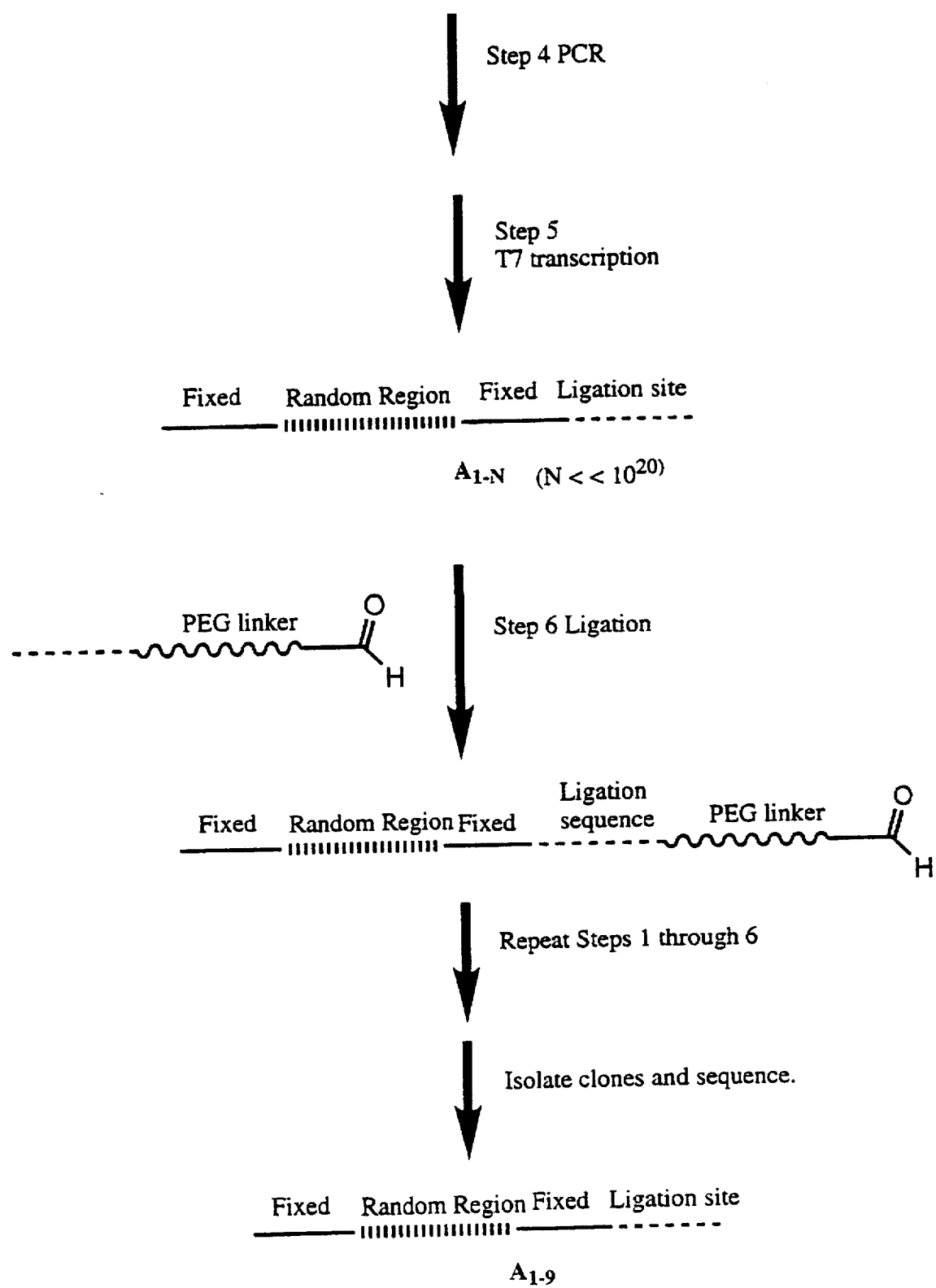

Another reaction type useful in synthetic and biosynthetic chemistry is the Aldol condensation. The basic concepts discussed for the Diels-Alder reaction apply to the Aldol reaction wherein one or more aldehyde is one reactant and one or more ketone is another reactant. A logical variation of how to tailor Parallel SELEX to an Aldol condensation is described in the following example and FIG. 4A–4C. The RNA (or DNA) is comprised of a 3' and 5' fixed region for transcription. Attached to the RNA is a PEG linker (20–50 ethylene units long) which in turn has a first reactant aldehyde connected. The first reactant aldehyde will serve as the electrophile in the Aldol reaction by virtue of its greater reactivity as compared to a second reactant ketone. The pool of RNA sequences labeled A would fold up into different structural motifs. Second reactant ketones labeled $B_{1-10}$ with different chemical groups $R^1$ and $R^2$ would be treated with A in Step 1 of FIG. 4A. The RNA would need to contain an amine capable of adding to the carbonyl of the ketones and forming an enamine as denoted by $C_{1-10}$, $D_{1-10}$, $E_{1-10}$ and $F_{1-10}$. The shape of the RNA will determine whether the E- or Z- enamine is formed. The enamine would then serve as a nucleophile in the Aldol reaction with the appended aldehyde. The steric and electronic environment of the RNA surrounding the enamine will determine the degree of enantioselectivity observed for a given RNA sequence.

For the purposes of this example the Aldol condensation products $G_{1-10}$, $H_{1-19}$, $G^*_{1-10}$ and $H^*_{1-10}$ are derived from attack of the first reactant aldehyde from the same face. It is possible to form the same product by approach from the opposite face if a different enamine and relative orientation of the first reactant aldehyde occurs and this is likely to happen. It is important that for the two new chiral centers being formed that all forty products are represented as $G_{1-10}$, $H_{1-10}$, $G^*_{1-10}$ and $H^*_{1-10}$. Aldol products $G_{1-10}/G^*_{1-10}$ are enantiomers as are $H_{1-10}/H^*_{1-10}$.

In water the imine linkage of $G_{1-10}$, $H_{1-10}$, $G^*_{1-10}$ and $H^*_{1-10}$ will be reversible and hydrolyzed to give the corresponding 13-ketoalcohol products. Selecting the highest affinity β-ketoalcohol desirable products will be accomplished by partitioning the resulting product library with the protein target linked to biotin or a column support. After allowing for equilibration the selected RNA is amplified by standard SELEX techniques as shown by Steps 3–5 in FIG. 4. The RNA obtained after Step 5 when folded up is the active catalyst for the formation of the Aldol β-ketoalcohol products denoted by $G_{1-9}$.

Once a maximum level of facilitation is achieved or the affinity of binding to the target levels off, the facilitating RNA associated with desirable products would be cloned and sequenced. The facilitating RNA could then be prepared separately and the synthesis of their corresponding β-ketoalcohol desirable products performed on a scale sufficient for isolation followed by structural characterization by spectroscopic methods.

As with the Diels-Alder example, the array of first reactant aldehydes employed in the Parallel SELEX could be expanded by attaching different first reactant aldehydes to the PEG linker and encoding the ligation sequence for which first reactant aldehydes were attached to which nucleic acids.

Figure 5:
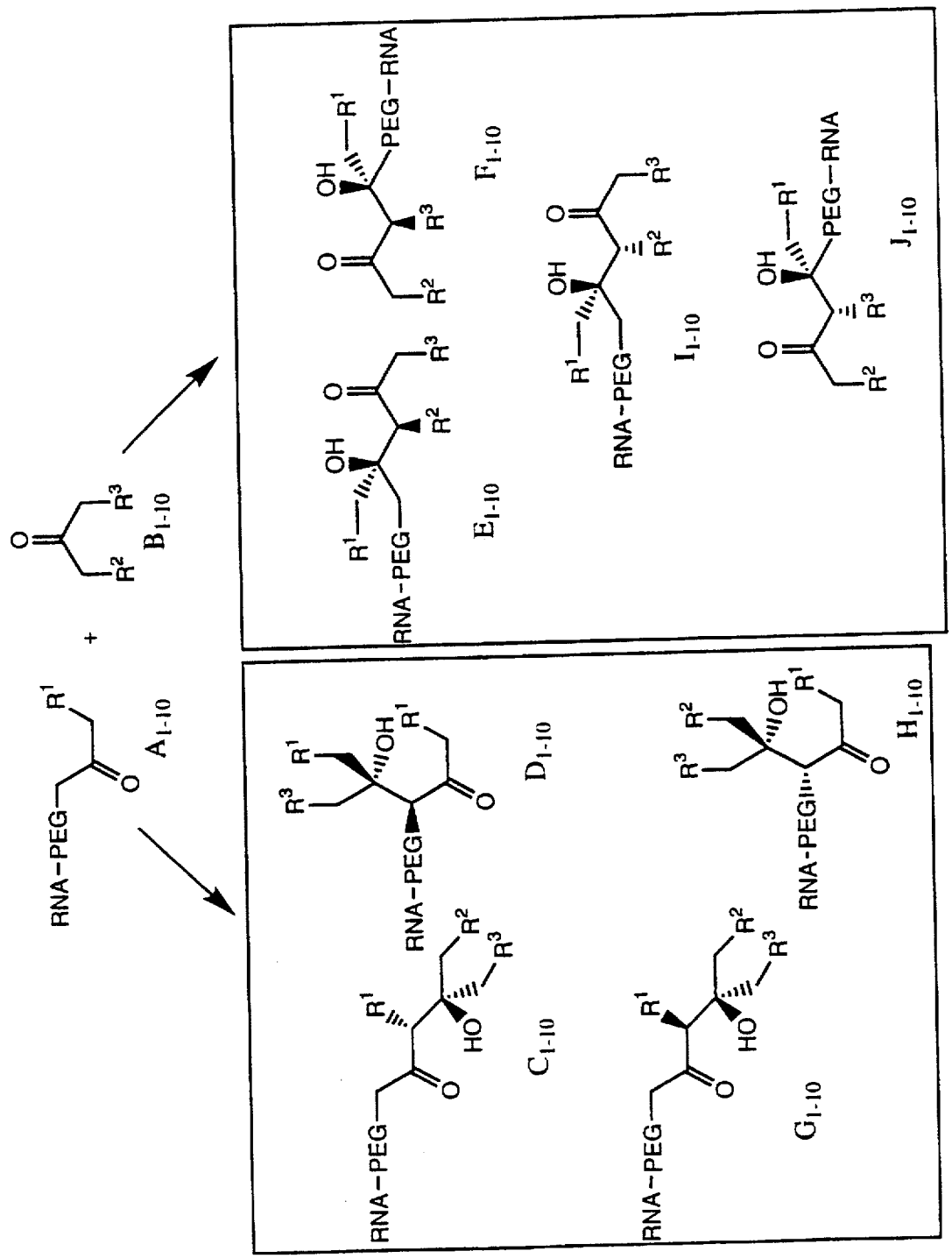
FIG. 5 depicts the impact of the mixed Aldol reaction described in FIGS. 4A–4C on structural diversity of the products. Only diastereomers am shown and each structure would have a corresponding enantiomer.

From the Diels-Alder reaction example discussed above, a factor of 4 is obtained for the creation of two stereocenters. However, the Aldol condensation has the potential to form many more possibilities than this. Consider the mixed Aldol reaction where two ketones are used as first and second reactants that have comparable electrophilicity at the carbonyl carbon and similar nucleophilicity at the α-carbons (FIG. 5). Typically in organic synthesis this type of reaction is avoided because a very complex mixture of products can result. In the Parallel SELEX strategy this increase in diversity could be of added benefit. Structures C, D, E, F, G, H, I and J are all different diastereomers. Each of these products has a corresponding enantiomer, which means that for the mixed Aldol condensation reaction of FIG. 4, 1600 products with different structures would be formed from the original 20 ($A_{1-10}$ and $B_{1-10}$).

c. [2+2+2] Cyclotrimerization Reactions

Parallel Selection and coevolution of both the facilitating RNA and the desirable product is not limited to the formation of products having structures that create chiral centers. Many important medicinal compounds contain achiral aromatic groups with appended chiral substituents. One of the most powerful methods for the construction of products comprising aromatic ring systems (benzenes, naphthalenes, pyridines etc.) is cyclopentadienyl cobalt (CpCo) mediated cyclotrimerization of first, second and third reactant alkynes. It should be noted that [2+2+2] cyclotrimerization is not limited to alkyne reactants and that non-aromatic six membered ring products can be assembled by combining alkyne and alkene reactants.

The example discussed here includes the embodiment of the invention where an organometallic catalyst is incorporated in the RNA (or DNA) and its use in Parallel SELEX. Steps 1–6 described above and shown in FIGS. 2 and 4 are general to all Parallel SELEX so only the impact of cyclotrimerization on the potential number of product structures formed will be discussed here. For cyclotrimerization of three alkyne reactants to form a product including a benzene ring the maximum number of possibilities is obtained using three different alkyne reactants that have different substituents attached to each end of each reactant (depicted in FIG. 6).

Figure 6:
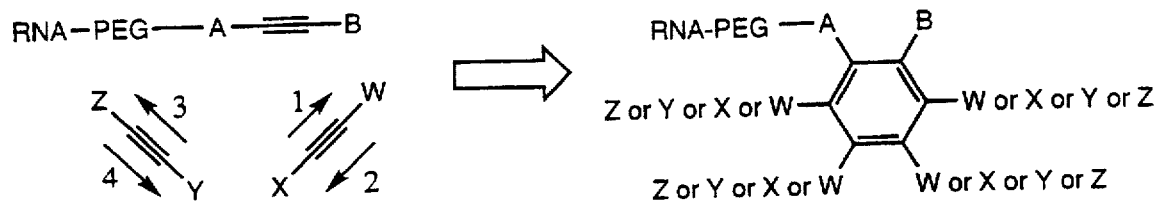
FIG. 6 depicts a matrix of possibilities for the assembly of benzene compounds by cyclotrimerization of three alkynes in the top panel. In the bottom panel, the mechanism of cyclotrimerization of alkynes is depicted. Only one of the possible products is shown.
Figure 6:
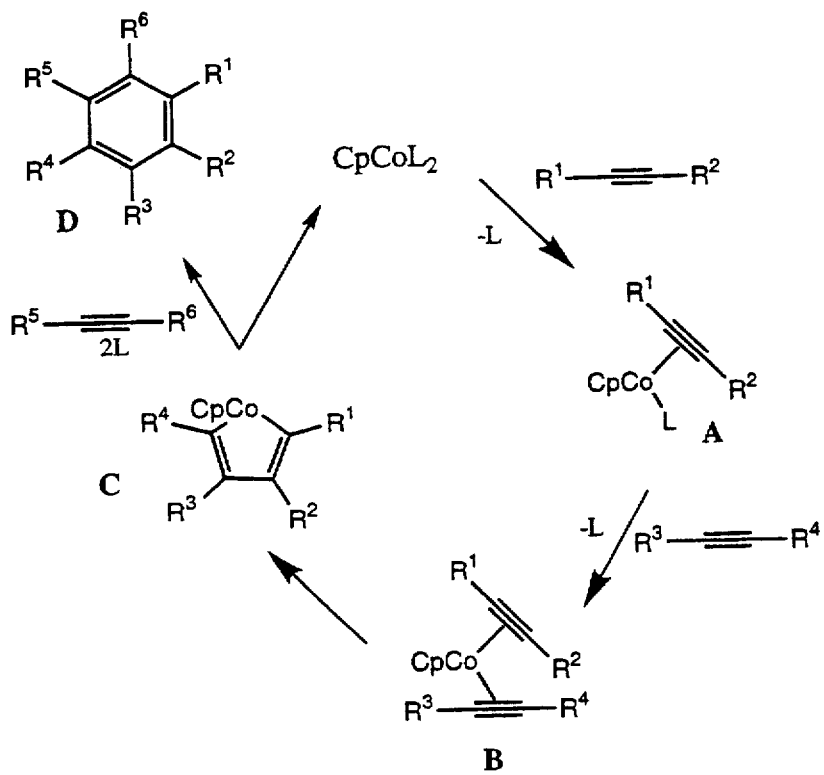

For a cyclotrimerization of alkyne reactants as shown in FIG. 6 there are $4MN^2$ possible regioisomer products where M=the number of nonsymmetric alkyne first reactants attached to the RNA and N=the number of free nonsymmetric alkyne second and third reactants that are contacted with the RNA-first reactant mixture. FIG. 6 shows the matrix of possibilities for only 3 alkyne reactants, where the first reactant is attached to the RNA and the second and third reactants are free. If Parallel SELEX is expanded to include 10 alkyne first reactants attached to the RNA molecules and 10 second and third reactants there could be 4,000 benzene products made.

The mechanism of CpCo catalyzed cyclotrimerization of alkyne reactants is given in the bottom panel of FIG. 6. By attaching CpCo (or another metal complex capable of cyclizing alkynes) to an oligonucleotide as described above it may be possible to form a cyclotrimerizing facilitating RNA. RNA structures that are folded up around the organometallic center will provide a pocket that will impart selectivity in either of the bond forming steps depicted in FIG. 6, B–>C or C–>D. Employing the partitioning of Parallel SELEX should provide the specificity for the products. On cloning and benzene products. On cloning and preparation of sufficient amounts of the facilitating RNA the coevolved aromatic product(s) may be prepared by treating the RNA with the mixture of alkyne reactants used in selection. The aromatic product obtained then can be structurally characterized by conventional methods.

d. Retrosynthetic Strategies

Figure 7:
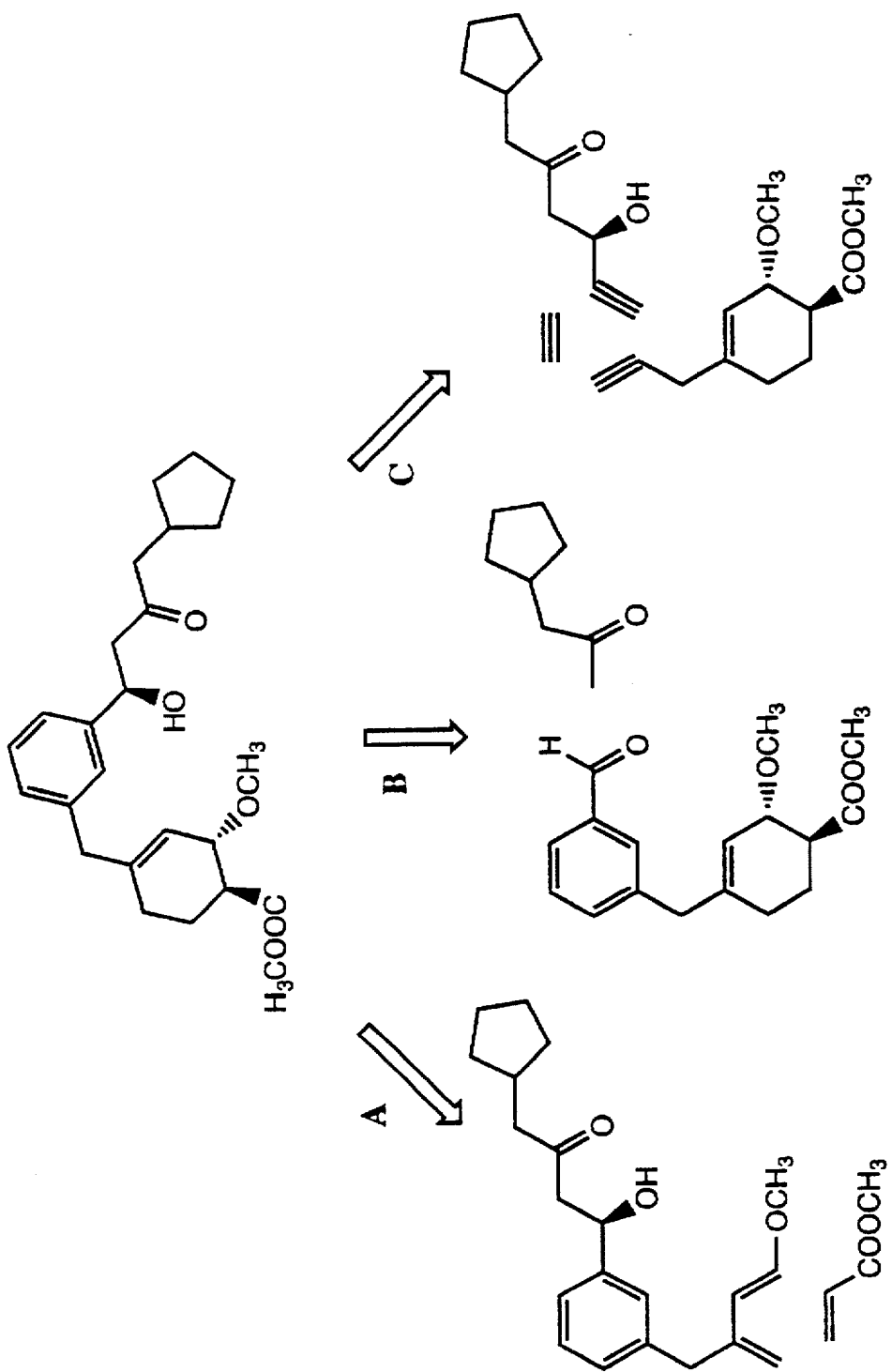
FIG. 7 depicts a possible strategy for retrosynthesizing a typical product of the invention.

In general it is envisaged that all Parallel SELEX schemes will have in common Steps 1–6 as described above and by FIGS. 2 and 4. Different chemistries will only change the type and number of products formed. When considering which chemistry or chemistries is best to include in Parallel SELEX it can be valuable to perform a retrosynthetic analysis on the structural product class of interest. Consider FIG. 7 and the possible disconnections for the product shown. Disconnection A would involve the Diels-Alder transformation and B the Aldol condensation. Both of these bond forming reactions were discussed above. There are many other disconnections that could be made for this product. In general, retrosynthetic strategies that include ring forming product transformations are desirable because the greatest number of bonds or stereocenters are formed. When considering which types of reactions are most powerful for Parallel SELEX other factors may need to be considered. For example, the availability of reagents and the reactivity and stability of the oligonucleotides under the reaction conditions. Of significant importance is the number of possible stereo or regioisomer products that may be formed. While the Diels-Alder and Aldol condensation reactions have the potential to create a large number of products as a result of the formation of new stereocenters, the retrosynthetic path C can provide a significant number of regioisomer products. It is contemplated that the invention can include several chemical reactions, involving one or more facilitating nucleic acids and two or more different reactants, either simultaneously or sequentially, to make the products of the invention.

IV. Administration and Uses

Applications of the desirable products of this invention include various therapeutic, prophylactic, diagnostic, and cosmetic uses. Any use where a chemical product could be desirable is within the scope of this invention. Specific classes of conditions include, but are not limited to intimation, cardiovascular disorders, neoplastic conditions, metabolic disorders, parasitic diseases and infectious diseases. More specifically, the products of the invention are useful in treating or preventing cancer, angina, arthritis, asthma, allergies, rhinitis, shock, inflammatory bowel disease, low blood pressure, and systemic treatment of pain and inflammation, local trauma such as wounds, burns, rashes.

The desirable products of this invention, once identified by the Parallel SELEX method, can be produced for manufacture by conventional chemical synthesis routes or by using the facilitating nucleic acid to mediate the reaction between reactants. The products of the invention may contain an asymmetric atom. The asymmetric atom can be selected from carbon, phosphorous, silicon, sulfur, to name a few. Thus, the invention includes the individual stereoisomers, and the mixtures thereof. The individual isomers may be prepared or isolated by methods known in the art.

The desirable products can be administered by any method known to one of ordinary skill in the art. The modes of administration include, but are not limited to, enteral (oral) administration, parenteral (intravenous, subcutaneous, and intramuscular) administration, topical application, and mucosal (nasal, respiratory, etc.) application.

The method of treatment according to this invention comprises administering internally or topically to a subject in need of treatment an effective amount of the desirable product. Doses of desirable products in the inventive method and pharmaceutical compositions containing same are an efficacious, nontoxic quantity generally selected from the range of 0.01 to 500 mg/kg of desirable product, preferably 0.1 to 50 mg/kg. Persons skilled in the art using routine clinical testing are able to determine optimum doses for the particular ailment being treated. The desired dose is generally administered to a subject from 1 to 6 or more times daily, intravenously, orally, rectally, parenterally, topically, or by inhalation. The efficacy of the desirable products of this invention can be determined by standard techniques known to one of ordinary skill in the art.

The preparation of products for administration in pharmaceutical preparations may be performed in a variety of methods well known to those skilled in the art. Appropriate pharmaceutically acceptable salts within the scope of the invention are those derived from mineral acids such as hydrochloric acid, hydrobromic acid, phosphoric acid, nitric acid, and sulfuric acid; and organic acids such as tartaric acid, fumaric acid, lactic acid, oxalic acid, ethylsulfonic acid, p-toluenesulfonic acid, and the like, giving the hydrochloride, sulfate, phosphate, nitrate, methanesulfonate, tartrate, benzenesulfonate, p-toluenesulfonate, and the like, salt, respectively.

Desirable products of the invention may be formulated for parenteral administration in aqueous injection solutions which may contain antioxidants, buffers, bacteriostatic agents, solubilizing agents, chemoprotectants, etc. Extemporaneous injection solutions may be prepared from sterile pills, granules, or tablets which may contain diluents, dispersing and surface active agents, binders and lubricants which materials are all well known to the ordinary skilled artisan.

In the case of oral administration, fine powders or granules of the desirable product may be formulated with diluents and dispersing and surface active agents, and may be prepared in water or in a syrup, in capsules or cachets in the dry state or in a non-aqueous suspension, where a suspending agent may be included. The desirable products may also be administered in tablet form along with optional binders and lubricants, or in a suspension in water or syrup or an oil or in a water/oil emulsion or in a sustained release form from biodegradable or bioerodible polymers and may include flavoring, preserving, suspending, thickening, and emulsifying agents. The granules or tablets for oral administration may be coated or other pharmaceutically acceptable agents and formulation may be utilized which are all known to those skilled in the pharmaceutical art.

Solid or liquid carriers can also be used. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Ointments and creams are prepared using various well known hydrophilic and hydrophobic bases. Topical reservoirs suitably are prepared using known polymeric materials such as various acrylic-based polymers selected to provide desired release characteristics. Suppositories are prepared from standard bases such as polyethylene glycol and cocoa butter. Liposomes can also be used a carriers for the products of the invention.

Additionally, the desirable products of this invention can find use as agricultural agents. Specifically, the desirable products can be herbicides, pesticides, growth regulators, etc. The use and administration of the products of the invention for agricultural purposes is known by one of ordinary skill in the art. The products of the invention can also be used in chemical manufacturing processes.

EXAMPLES

The following examples are illustrative of preferred embodiments of methods of preparation and products of the invention and are not to be construed as limiting the invention thereto.

Example One

Use of Unmodified RNA to Facilitate a Diels-Alder Reaction Synthesizing a PEG linker A polyethylene glycol (PEG) linker was synthesized to act as a spacer between the nucleic acids (in this case 40N8 RNA)(SEQ ID NO:2) and the first reactant (in this case maleimide). The scheme for the synthesis of the linker is shown below.

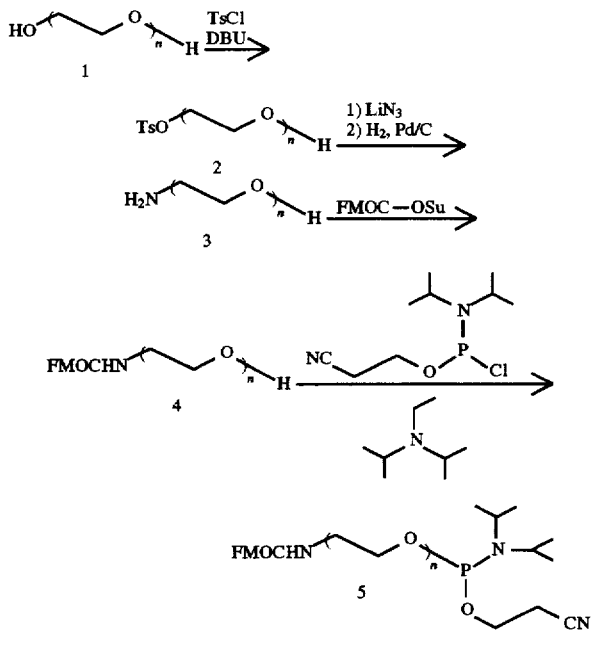

Synthesis of tosylated-PEG Ts-PEG) (2)—Polyethylene glycol 1, 1.0 g (0.670 mmol, average molecular weight 1500) was dissolved in 15 mL of dry THF and the solvent removed in vacuo. To the remaining residue, dissolved in 15 mL of dry THF was added 52 mg (0.335 mmol) of DBU followed by 64 mg (0.335 mmol) of p-toluenesulfonyl chloride. The mixture was stirred under argon at room temperature for 10 days during which time a white precipitate formed. After 10 days the reaction mixture was filtered and the solvent was removed in vacuo. Purification of the monotosylated product by flash silica gel chromatography (7% MeOH/CH$_2$Cl$_2$) yielded 320 mg (58%) of a slightly yellow solid (R$_f$=0.31). The product was identified on the basis of its $^1$H NMR spectrum.

Synthesis of Amino-PEG (3)—In 2 mL of dry DMF was dissolved 400 mg (0.243 mmol) of Ts-PEG (2) followed by 119 mg (2.43 mmol) of lithium azide. With stirring and under an argon atmosphere the reaction mixture was heated to 80° C. for 5 hours. After coming to room temperature, the mixture was filtered through a silica pad, and the pad washed with 10% MeOH/CH$_2$Cl$_2$ until no product was detected in the eluent. The combined filtrate was evaporated to dryness under reduced pressure. The remaining residue was dissolved in 4 mL of MeOH to which was added 30 mg of 5% Pd/C and the solution was stirred under one atmosphere of hydrogen for 16 hours. The mixture was then filtered through celite. The celite pad was washed with MeOH, the filtrate combined and the solvent evaporated under reduced pressure to give an off-white solid. Purification by flash silica gel chromatography (12% MeOH.NH$_3$/CH$_2$Cl$_2$) yielded 279 mg (77%) of the desired amino-PEG product 3 (R$_f$=0.38, 15% MeOH.NH$_3$/CH$_2$Cl$_2$) as a white solid.

Synthesis of FMOC-PEG (4)—Amino-PEG (3) was dried by dissolving 840 mg (0.563 mmol) in 75 mL of dry THF followed by removal of the solvent by rotary evaporation. Under an argon atmosphere the amino-PEG was then dissolved in 50 mL dry THF, treated with 190 mg (0.563 mmol) of 9-fluorenylmethyl succinimidyl carbonate and the solution stirred at room temperature under argon for 2 hours. The solvent was then removed by rotary evaporation and the product purified by flash silica gel chromatography (8% MeOH/CH2Cl$_2$) to give 863 mg (92%) of a white solid (R$_f$=0.28, 10% MeOH/CH$_2$Cl$_2$).

Synthesis of FMOC:PEG phosphoramidite (5)—FMOC-PEG (4) was dried by dissolving 173 mg (0.104 mmol) in 25 mL of dry THF followed by removal of the solvent by rotary evaporation. Under an argon atmosphere, the FMOC-PEG was then dissolved in 25 mL of dry CH$_2$Cl$_2$, treated with 34.8 mL (0.208 mmol) of diisopropylethyl amine followed by 36.2 mL (0.156 mmol) of 2-cyano N,N-diisopropylchlorophosphoramidite. The mixture was stirred for 1 hour at room temperature. The solvent and excess base was then removed under reduced pressure. The desired phosphoramidite product was purified by flash silica gel chromatography (8% MeOH/CH$_2$Cl$_2$) to yield 190 mg (97%) of a white solid (R$_f$=0.30, 10% MeOH/CH$_2$Cl$_2$).

DNA-PEG Conjugation and First Reactant Addition

The protected PEG linker synthesized above is then conjugated to the 5' end of a DNA 10-mer (to facilitate ligation with random RNA) followed by coupling of the first reactant (in this case maleimide) as shown in the scheme below.

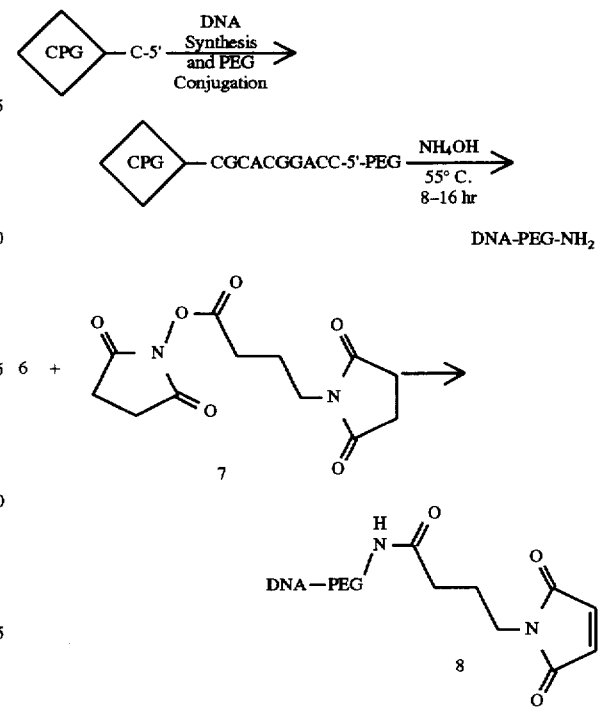

An applied Biosystems DNA synthesizer is used to synthesize the DNA 10-mer (5'-CCAGGCACGC) (SEQ ID NO. 1) and conjugate the FMOC-PEG phosphoramidite synthesized above in one procedure using standard phosphoramidite chemistries shown above. The DNA-PEG conjugate is cleaved from the CPG (controlled pore glass) solid phase support and fully deprotected using the standard overnight incubation in concentrated ammonium hydroxide to give the DNA-PEG free amine species 6. Any substrate can then be added to the end of the PEG chain using a variety of reactions. For example, a maleimide dienophile for a Diels-Alder reaction is appended by reacting the amino DNA-PEG with the maleimide activated ester 7 to give the amide 8.

Producing Random RNA Pool having a 5' Monophosphate

A random sequence 40N8 RNA pool (SEQ ID NO. 2) was prepared using standard SELEX strategies and techniques from a synthetic, random sequence single-stranded DNA (ssDNA) template obtained from Operon (Alameda, Calif.). The random region was generated by utilizing a mixture of the four nucleotides (the molar ratios of which are adjusted to yield a 1:1:1:1 ratio of incorporated nucleotides) during oligonucleotide synthesis. The ssDNAs contained 40 nucleotides of contiguous random sequence flanked by defined 5' and 3' ends that permit primer hybridization. The double-stranded DNA (dsDNA) molecules, synthesized by Taq Polymerase, have a T7 RNA Polymerase promoter at the 5' end to facilitate transcription.

Each transcription reaction consisted of 100 pmoles of 40N8 dsDNA combined with 80 µl 5X T7 RNA Polymerase Buffer (200 mM Tris-pH 8.0, 60 mM MgCl$_2$, 5 mM Spermadine, 25 mM DTT, 20% Glycerol, 0.01% Triton-X-100), 40 µl 10 mM GTP, 40 µl 10 mM CTP, 40 µl 10 mM ATP, 40 µl 10 mM UTP, 40 µl 500 mM GMP, 8 µl RNasin (Promega, 40,000 Units/mL), 24 µl T7 RNA Polymerase (New England Biolabs, 50,000 Units/mL), and dH$_2$O to a final volume of 400 µl.

After an overnight incubation at 37° C., the 5' monophosphate RNA was purified using a 8% denaturing polyacrylamide gel. The 5' monophosphate is necessary for ligation of the RNA to the DNA portion of the linker sequence as described below.

Ligating the Random RNA to DNA-PEG-maleimide

A random sequence RNA pool was generated as described above. A DNA 10-mer (SEQ ID NO. 1) and DNA bridge oligo (5'-CTTGTCTCCCGCGTGCCTGG) (SEQ ID NO. 3) used in the ligation reaction were obtained from Operon (Alameda, Calif.) and gel purified before use. One hundred pmoles of the random 40N8 RNA (SEQ ID NO. 2) was end-labeled by dephosphorylation with Bacterial Alkaline Phosphatase (Gibco BRL) and subsequent phosphorylation with T4 Polynucleotide Kinase (New England Biolabs) and γ-[$^{32}$P] ATP.

The ligation reaction contains 50 pmoles of random 40N8 RNA, approximately 60,000 CPM of random, 5'-end labeled 40N8 RNA, 100 pmoles DNA-PEG-Maleimide, 150 pmoles DNA bridge oligo, 2.5 mL 10X T4 DNA Ligase Buffer (50 mM Tris-pH 7.8, 10 mM MgCl$_2$, 10 mM DTT, 1 mM ATP, 25 mg/ml Bovine Serum Albumin 0.5 µl RNasin (Promega, 40,000 Units/mL), T4 DNA Ligase to a final concentration of 1.2 Weiss Units/mL (New England Biolabs), and dH$_2$O to a final volume of 25 µl. The 1.2 Weiss Units/mL were obtained by converting New England Biolabs' unit definition to Weiss Units using the conversion factor found in any of their catalogs (1 NEB=0.015 Weiss Units).

All components except RNasin and T4 DNA Ligase were mixed, incubated at 70° C. for 3 minutes and slow-cooled to less than 37° C. RNasin and T4 DNA Ligase were then added, and the mixture was incubated for 90 minutes at 37° C. After incubation, RNA loading buffer was added and the mixture was heated to 70° C. for 3 minutes and then loaded onto a pre-heated 8% denaturing polyacrylamide gel. Ligation yields were obtained by autoradiography. The resulting RNA-DNA-PEG-maleimide is the nucleic acid-reactant test mixture.

Preparation of Biotinylated Diene Conjugate

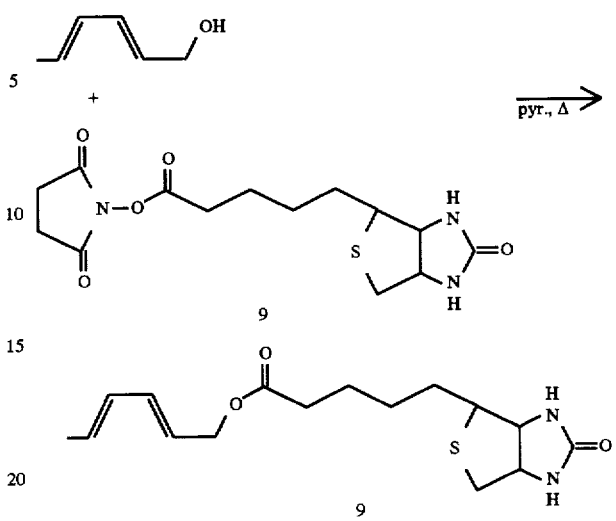

NHS-biotin (Pierce, 99.3 mg, 0.291 mmol) and 2,4-hexadien-1-ol (66.2 mg, 2.3 eq.) were combined in 10 mL of dry pyridine under argon at 0° C. and stirred in the dark overnight while warming to ambient temperature. Monitoring of the reaction mixture by TLC (50% EtOAc/Hexanes) indicated slow reaction and the solution was then brought to reflux under argon overnight. Removal of the solvent in vacuo followed by successive chromatography on flash silica gel with 5% MeOH/EtOAc then 6% MeOH/CH$_2$Cl$_2$ afforded pure product 9, which was characterized on the basis of its $^1$H and $^1$H-$^1$H COSY NMR spectra.

The Chemical Reaction

The nucleic acid-reactant test mixture prepared above (RNA-DNA-PEG-maleimide) is reacted with the second reactant (biotinylated diene) under the following conditions. One-two nmol (~50,000 cpm) of nucleic acid-reactant test mixture is dissolved in 50 µL of reaction buffer (10 mM MES, 200 mM NaCl, pH 6.5), alternatively the reaction buffer can be (10 mM Tris, 300 mM NaCl, pH 7.0). The mixture is heated to 70° C. for 5 minutes. MgCl$_2$ is then added to a final concentration of 100 µM and 10 µM respectively and the solution is allowed to slowly come to room temperature (approximately 10 minutes). The biotinylated diene is then added to a final concentration of 1 mM, and the mixture is allowed to incubate at room temperature for 12 hours. The solution is then loaded on an immobilized streptavidin column and the column washed extensively with reaction buffer containing 10 µM MgCl$_2$. The bound RNA is liberated from the column matrix by treatment with proteinase K followed by washing the column with reaction buffer. Alternatively the RNA can be reverse transcribed while still bound to the resin or a disulfide linked biotin-diene substrate can be used in which case the RNA is eluted from the column using 50 mM DTT. Enrichment of the pool is followed by the number of cpm's eluted following standard proteinase K treatment. The eluted RNA is then reverse transcribed, the resulting cDNA PCR amplified, and the dsDNA transcribed as in typical SELEX experiments. The DNA-PEG-maleimide conjugate is ligated to the RNA as described above and the process repeated until the quantity of the resulting product is significant enough to determine the structure thereof.

Example Two

Use of Unmodified RNA and Metals in Solution to Facilitate a Diels-Alder Reaction The procedure followed for Example One is repeated exactly, with the inclusion of the metal ions aluminum(III) and cobalt(II) in the reaction solution.

Example Three

Use of Modified RNA (incorporating pyridine-modified UTP), to Facilitate a Diels-Alder Reaction The nucleic acids of this invention can be modified by various procedures described previously. One example of a modified nucleic acid is given where UTP molecules have been modified to incorporate a pyridine-type residue at the 5-position. The pyridine-modified UTP is incorporated into the random RNA described previously. The modified RNAs are attached to a reactant through a PEG linker and used to facilitate a Diels-Alder reaction.

The following procedure was followed to synthesize a uridine triphosphate (UTP) derivative that has a pyridine-type residue attached to the 5-position of the base.

Preparation of pyridyl carboxamide modified UTP ated three times, then pressurized to 50 psi CO and sealed. The flask was stirred vigorously while heating to 70° C. After 2 hrs., visible plating of the palladium had begun. The flask was stirred an additional 18 hrs., cooled and vented, and the solution evaporated to a yellowish oil. Chromatography on silica gel with 8–10% MeOH/CH$_2$Cl$_2$ gradient elution afforded 0.177 g (78%) of 10 as a white solid. Characterized by its $^1$H, $^{13}$C NMR spectra. Analytical samples could be obtained by recrystallization from methanol.

Triphosphate preparation

The triphosphate was prepared by the procedure of Ludwig and Eckstein (*J. Org. Chem.* 1989, 54, 631–635) using the 5'-hydroxyl modified uridine prepared above. The triphosphate was purified by passage of the reaction mixture in distilled water through an anion exchange column (Sephadex DEAE) with 0.05–1.00M TBK (triethyl ammonium bicarbonate) buffer solution. Lyophilization of the fractions which contained the triphosphate gave the isopropylidene-protected triphosphate, which was characterized by its $^{31}$P NMR spectrum. The isopropylidene protecting group was removed by heating the triphosphate in 5 mL of distilled water with 100 mg of Dowex 50WX8 resin (H$^+$ form) for 15 min. at 70° C., followed by neutralization with 2M TBK buffer (to pH 8). Final purification of this solution

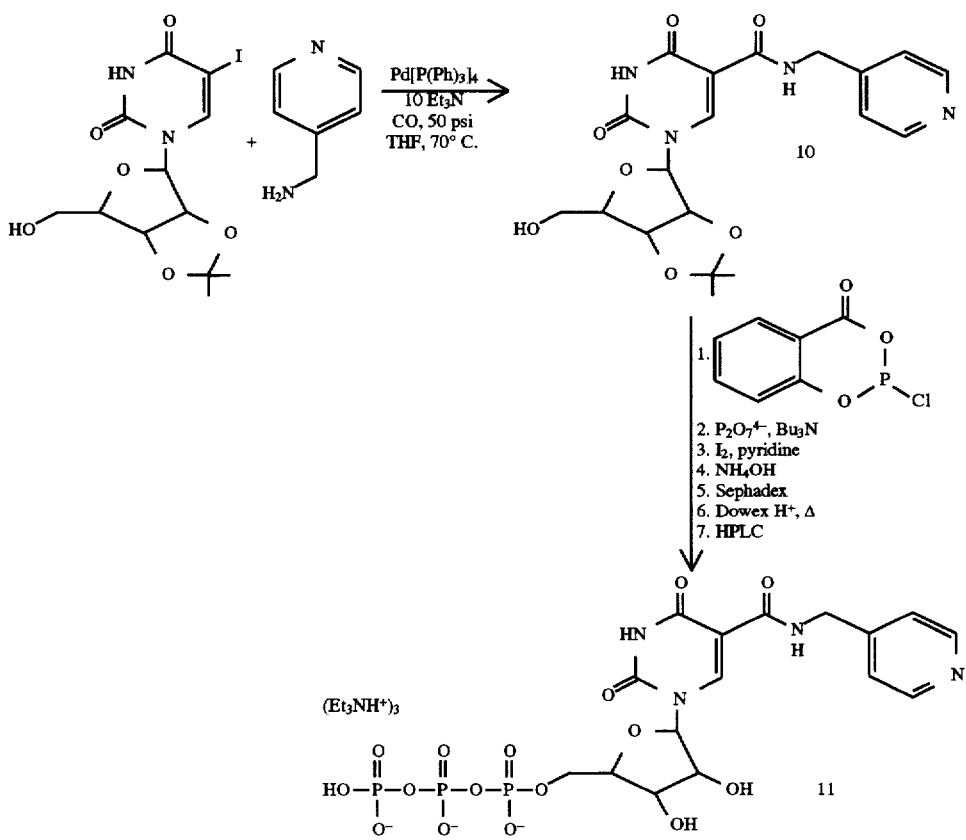

Carboxyamidation

A solution of 5-iodouridine-2',3'-isopropylidene (0.225 g, 0.545 mmol), Pd(PPh$_3$)$_4$ (0.1 eq., 56 mg), triethylamine (10 eq., 0.76 mL), and 4-(aminomethyl)-pyridine (4 eq., 0.23 mL) was prepared in 10 mL of dry THF under argon in a flame-dried glass bomb equipped with a teflon stopcock. The bomb was successively charged with 50 psi CO and evacuwas performed by reverse phase preparatory HPLC (C18 column) with 3–5% gradient of CH$_3$CN in 0.05M TBK buffer. The triphosphate thus prepared (11) was characterized on the basis of its $^1$H and $^{31}$P NMR spectra as the tris(triethylammonium) salt form and quantitated by UV absorbance (277 nm, $\epsilon$=14,600M$^{-1}$ cm$^{-1}$).

The reaction is continued as described in Example 1 above.

Example Four

Use of Modified RNA (incorporating histidine-modified UTP) to Facilitate the Cleavage of GRP The nucleic acids of this invention can be modified by various procedures described previously. One example of a modified nucleic acid is given where UTP molecules have been modified to incorporate a histidine-type residue at the 5-position. The histidine-modified UTP is incorporated into the random RNA (SEQ ID NO. 2) described previously The modified RNAs are attached to a reactant through a PEG linker and used to facilitate the cleavage of Gastrin Releasing Peptide (GRP).

Synthesizing histidine-modified UTP

The following procedure was followed to synthesize uridine triphosphate (UTP) molecules that have a histidine-type residue attached to the 5-position.

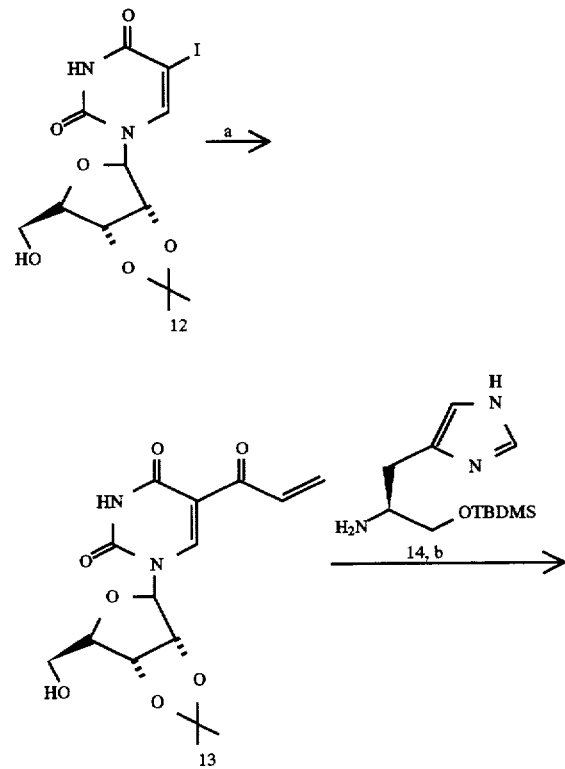

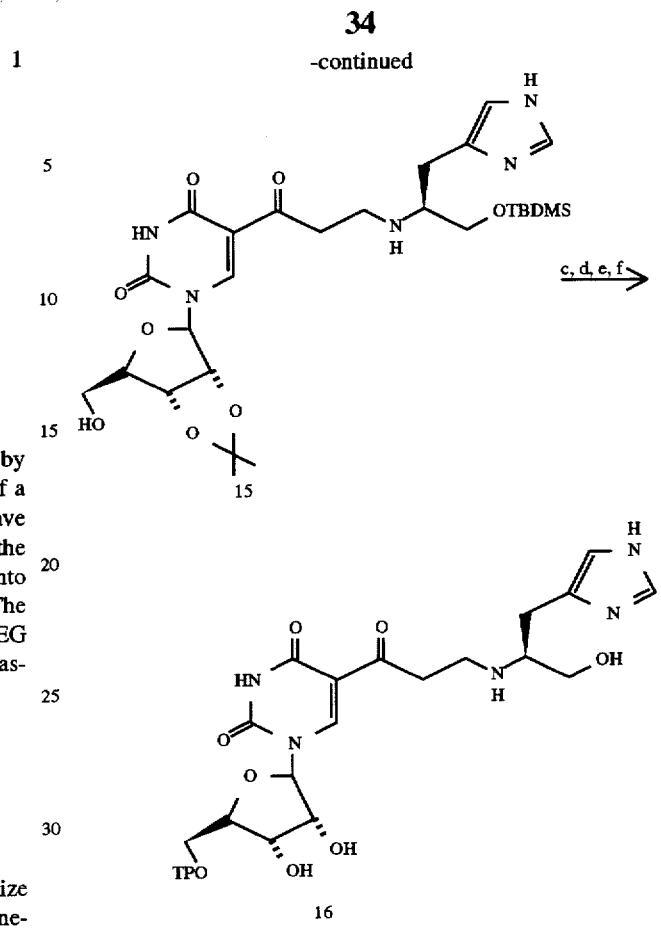

Key: (a) Pd(OAc)$_2$, CuI, PPh$_3$, CH$_2$CHSn(Bu)$_3$, CO, THF, 70° C., 5 h. (b) Hunig's base, DMF, RT, 1 h. (c) 2-chloro-4H-1,2,3-benze-dioxaphosphorin-4-one, P$_2$O$_7^{4-}$ (HNBu$_3$)$_2^{2+}$, pyridine, dioxane. (d)I$_2$, pyridine/H$_2$O (98:2). (e) NH$_4$OH. (f) Dowex 50w x8, H$_2$O, 70° C., 15 min.

Into a self-contained coupling apparatus, equipped with a pressure-equalizing addition funnel, in an inert atmosphere glove box was weighed 702.3 mg (2.0 mmol) 12, 44.9 mg (0.20 mmol) palladium acetate, 114.3 mg (0.60 mmol) copper(I)iodide, and 157.4 mg (0.60 mmol) triphenylphosphine. The apparatus was sealed, removed from the box, and 30 mL of anhydrous THF added to the round bottom portion of the apparatus via cannula. To the addition funnel portion was added via cannula an argon-purged solution of 0.643 mL (2.2 mmol) vinyltributyltin in 40 mL of anhydrous THF. The flask was successively evacuated and charged three times with CO, then heated at 70° C. for 1.0 h until the yellow solution became slightly orange. The vinyltributyltin solution was then added at a rate of 1 drop per 10 sec. The solution turned dark red after 5–10% of reagent addition. The solution was heated at 70° C. for 5 h, allowed to cool and concentrated in vacuo. The residue was dissolved in CH$_2$Cl$_2$, loaded onto a pad of silica, washed with 200 mL hexane, 200 mL CH$_2$Cl$_2$ and the product eluted with 5% CH$_3$OH/CH$_2$Cl$_2$. This eluent was concentrated and flash chromatographed on silica gel with 5% CH$_3$OH/CH$_2$Cl$_2$ to yield 0.294 g of 13 as a white solid.

Histidinol Michael addition adduct

TBDMS protected histidinol 14—To a stirred solution of 205 mg (5.1 mmol) of NaH washed 3× with hexane, under argon, in 3.0 mL DMF was added in portions 500 mg (2.3 mmol) of histidinol dihydrochloride, resulting in moderate gas evolution. The solution was stirred for 1.5 h, then 1.8 mL (23 mmol) of anhydrous pyridine and 693.0 mg (4.6 mmol) of TBDMSCl was added. The solution was stirred for 1.5 h, concentrated in vacuo and flash chromatographed on silica with 15% $CH_3OH.NH_3/CH_2Cl_2$ to yield 14.

Michael adduct 15—To a stirred solution of 167.9 mg (0.6 mmol) 13 in 10 mL of anhydrous DMF was added 0.105 mL (0.6 mmol) of diisopropylethylamine, then dropwise a solution of 185 mg (0.72 mmol) of 14 in 1.85 mL of anhydrous DMF. The solution was stirred for 1 h, concentrated in vacuo and flash chromatographed on silica gel with 15% $CH_3OH.NH_3$/ethyl acetate to yield 90.0 mg of 15 as a white solid, characterized on the basis of its $^1H$ NMR spectrum.

Triphosphate preparation

To a solution of 15 in dioxane/pyridine was added dropwise a solution of 2-chloro-4H-1,2,3-benzedioxaphosphorin-4-one in THF and the solution stirred for 20 min., then a 0.5M solution of bis(tributylammonium) pyrophosphate in DMF and tributylamine were added simultaneously. The solution was stirred for an additional 20 min., and a pyridine/water solution of $I_2$ added and the solution stirred for 20 min. Excess iodine was destroyed with 5% sodium bisulfite, stirred for 15 min., the solution concentrated, and hydrolyzed with concentrated ammonium hydroxide. The ammonia was removed/n vacuo, the remaining solution washed twice with $CH_2Cl_2$, once with ethyl acetate and concentrated in vacuo. The residue was dissolved in water and stirred with Dowex resin for 15 min. at 70° C. The solution was filtered, neutralized with 2M TBK buffer, loaded directly onto DEAE sephadex and eluted with a gradient of 0.05M triethylammonium bicarbonate buffer (TBK buffer) to 1.0M TBK buffer to yield product slightly contaminated with a salicylate species and a small mount with the TBDMS and isopropylidene protecting groups still intact. The material was again treated with dowex resin and purified on a reverse phase HPLC C18 column with a gradient of 0-5% acetonitrile in 0.05M TBK buffer over 15 min. to yield pure 16 by $^1H$, $^{13}C$ and $^{31}P$ NMR.

The experiment is continued as outlined in Example 1 above, however, rather than forming a cyclohexene product, the nucleic acid hydrolyzes the GRP protein.

---

We claim:

1. A non-naturally occurring facilitating nucleic acid that facilitates a bond formation reaction between a first reactant and a free reactant, wherein said bond formation reaction is selected from the group consisting of a condensation reaction, a hydrolysis reaction, a cycloaddition reaction, a conjugate addition reaction, an aldol condensation reaction, a cyclopropanation reaction, a hydrogenation reaction, and a cyclotrimerization reaction, wherein each reactant is comprised of a small organic molecule with a molecular weight in the range of 2 to 1000, and further wherein said first reactant is coupled to said nucleic acid.

2. A non-naturally occurring facilitating nucleic acid which increases the reaction rate of a bond formation reaction to form a product from a first reactant and a free reactant, wherein said bond formation reaction is selected from the group consisting of a condensation reaction, a hydrolysis reaction, a cycloaddition reaction, a conjugate addition reaction an aldol condensation reaction, a cyclopropanation reaction, a hydrogenation reaction, and a cyclotrimerization reaction, wherein each reactant is comprised of a small organic molecule with a molecular weight in the range of 2 to 1000, and further wherein said first reactant is coupled to said nucleic acid.

3. The facilitating nucleic acid of claim 1 wherein the nucleic acid is selected from the group consisting of single-stranded RNA, single-stranded DNA, and double-stranded DNA.

4. The non-naturally nucleic acid of claim 1 wherein the nucleic acid is selected from the group consisting of single-stranded RNA, single-stranded DNA, and double-stranded DNA.

* * * * *